United States Patent
Yen et al.

(10) Patent No.: US 11,833,122 B2
(45) Date of Patent: Dec. 5, 2023

(54) AMINONAPHTHOQUINONE COMPOUNDS FOR TREATMENT AND/OR PREVENTION OF FIBROSIS DISEASES

(71) Applicant: Calgent Biotechnology Co., Ltd., Taipei (TW)

(72) Inventors: Yun Yen, Arcadia, CA (US); Jing-ping Liou, Taipei (TW); Chien Huang Lin, Taipei (TW)

(73) Assignee: Calgent Biotechnology Co., Ltd., Taipei (TW)

( * ) Notice: Subject to any disclaimer, the term of this patent is extended or adjusted under 35 U.S.C. 154(b) by 0 days.

(21) Appl. No.: 15/776,698

(22) PCT Filed: Nov. 17, 2016

(86) PCT No.: PCT/US2016/062568
§ 371 (c)(1),
(2) Date: May 16, 2018

(87) PCT Pub. No.: WO2017/087695
PCT Pub. Date: May 26, 2017

(65) Prior Publication Data
US 2018/0325845 A1 Nov. 15, 2018

Related U.S. Application Data

(60) Provisional application No. 62/256,516, filed on Nov. 17, 2015.

(51) Int. Cl.
*A61P 1/16* (2006.01)
*A61K 31/4706* (2006.01)
(Continued)

(52) U.S. Cl.
CPC ............. *A61K 31/166* (2013.01); *A61K 9/20* (2013.01); *A61K 9/48* (2013.01); *A61K 31/40* (2013.01);
(Continued)

(58) Field of Classification Search
CPC ...... A61K 31/40; A61K 31/166; A61K 31/44; A61K 31/4706; A61P 11/00; A61P 1/16
See application file for complete search history.

(56) References Cited

U.S. PATENT DOCUMENTS

2005/0222043 A1  10/2005 Stangl et al.
2006/0128611 A1   6/2006 Lewis et al.
(Continued)

FOREIGN PATENT DOCUMENTS

CN  102875642 A  1/2013
CN  108135871 A  6/2018
(Continued)

OTHER PUBLICATIONS

Mehta et al (Int J Radiation Oncology Biol Phys, 2005; 63(1):5-24). (Year: 2005).*
(Continued)

*Primary Examiner* — Rayna Rodriguez
(74) *Attorney, Agent, or Firm* — Prosyla Group PC

(57) ABSTRACT

The invention relates to the use of a compound of Formula (I) as described herein and its effective dose in the prevention and/or treatment of fibrosis diseases. The compound can effectively prevent and/or treat a fibrosis disease without cytotoxicity or genotoxicity.

4 Claims, 17 Drawing Sheets

(51) Int. Cl.

| | | |
|---|---|---|
| *A61K 31/166* | (2006.01) | |
| *A61K 45/06* | (2006.01) | |
| *A61K 9/20* | (2006.01) | |
| *A61K 9/48* | (2006.01) | |
| *A61K 31/426* | (2006.01) | |
| *A61K 31/4409* | (2006.01) | |
| *C07C 15/00* | (2006.01) | |
| *A61P 11/00* | (2006.01) | |
| *A61K 31/40* | (2006.01) | |
| *A61K 31/404* | (2006.01) | |
| *A61K 31/415* | (2006.01) | |
| *A61K 31/416* | (2006.01) | |
| *A61K 31/4184* | (2006.01) | |
| *A61K 31/437* | (2006.01) | |
| *A61K 31/44* | (2006.01) | |
| *A61K 31/4402* | (2006.01) | |
| *A61K 31/4406* | (2006.01) | |
| *A61K 31/4453* | (2006.01) | |
| *A61K 31/47* | (2006.01) | |
| *A61K 31/495* | (2006.01) | |
| *A61K 31/4965* | (2006.01) | |
| *A61K 31/505* | (2006.01) | |
| *A61K 31/519* | (2006.01) | |
| *A61K 31/5375* | (2006.01) | |
| *A61K 9/00* | (2006.01) | |

(52) U.S. Cl.
CPC .......... *A61K 31/404* (2013.01); *A61K 31/415* (2013.01); *A61K 31/416* (2013.01); *A61K 31/4184* (2013.01); *A61K 31/426* (2013.01); *A61K 31/437* (2013.01); *A61K 31/44* (2013.01); *A61K 31/4402* (2013.01); *A61K 31/4406* (2013.01); *A61K 31/4409* (2013.01); *A61K 31/4453* (2013.01); *A61K 31/47* (2013.01); *A61K 31/4706* (2013.01); *A61K 31/495* (2013.01); *A61K 31/4965* (2013.01); *A61K 31/505* (2013.01); *A61K 31/519* (2013.01); *A61K 31/5375* (2013.01); *A61K 45/06* (2013.01); *A61P 11/00* (2018.01); *C07C 15/00* (2013.01); *A61K 9/0019* (2013.01)

(56) References Cited

U.S. PATENT DOCUMENTS

| | | |
|---|---|---|
| 2008/0090785 A1 | 4/2008 | Smyth et al. |
| 2011/0201609 A1 | 8/2011 | Lawrence et al. |

FOREIGN PATENT DOCUMENTS

| | | | |
|---|---|---|---|
| JP | 2006502998 A | 1/2006 | |
| JP | 2008522981 | 7/2008 | |
| WO | 2005089737 A2 | 9/2005 | |
| WO | WO-2006063154 A1 * | 6/2006 | ........... A61K 9/0019 |
| WO | WO-2017014788 A1 * | 1/2017 | ................ A61P 3/10 |

OTHER PUBLICATIONS

Patani et al (Chem Rev, 1996; 96:3147-3176) (Year: 1996).*
Antoniu (Expert Opin Investig Drugs, 2006; 15(7):823-828) (Year: 2006).*
Rosenbloom et al (Human fibrotic diseases: current challenges in fibrosis research. Fibrosis; 2017 pp. 1-23) (Year: 2017).*
Pulmonary Fibrosis News, (https://pulmonaryfibrosisnews.com/pulmonary-fibrosis-prevention/, Wayback Machine Internet Archive Date Mar. 13, 2016, obtained from the internet Oct. 27, 2022) (Year: 2016).*
Abstract of Xu, K., et al., "Design and synthesis of naphthoquinone derivatives as antiproliferative agents and 20S proteasome inhibitor," Bioorganic & Medicinal Chemistry Letters, vol. 22, Issue 8, Apr. 15, 2012, pp. 2772-2774.
Abstract of Pingaew, R., et al., "Novel 1,4-naphthoquinone-based sulfonamides: Synthesis, QSAR, anticancer and antimalarial studies," Eur J Med Chem., Oct. 20, 2015;103:446-59.
Extended European Search Report in corresponding EP Application No. 16867152.7, dated Jun. 5, 2019, in 10 pages.
Lawrence, Harshani R., et al. "Synthesis and biological evaluation of naphthoquinone analogs as a novel class of proteasome inhibitors." Bioorganic & Medicinal Chemistry 18.15 (2010): 5576-5592.
Carroll, F.I., "Preparation of Some Sufonamide and Diaminodiphenyl Sulfone Analogs of 1,4-Naphthoquinone1", J. Med. Chem., (1969), vol. 12, No. 1, pp. 187-189.
Office Action dated Aug. 6, 2021 in Japan Patent Application No. 2018-525670.
Office Action dated Mar. 15, 2021 in China Patent Application No. 201680067312.1.
Office Action dated Sep. 23, 2020 in Japan Patent Application No. 2018-525670.

\* cited by examiner

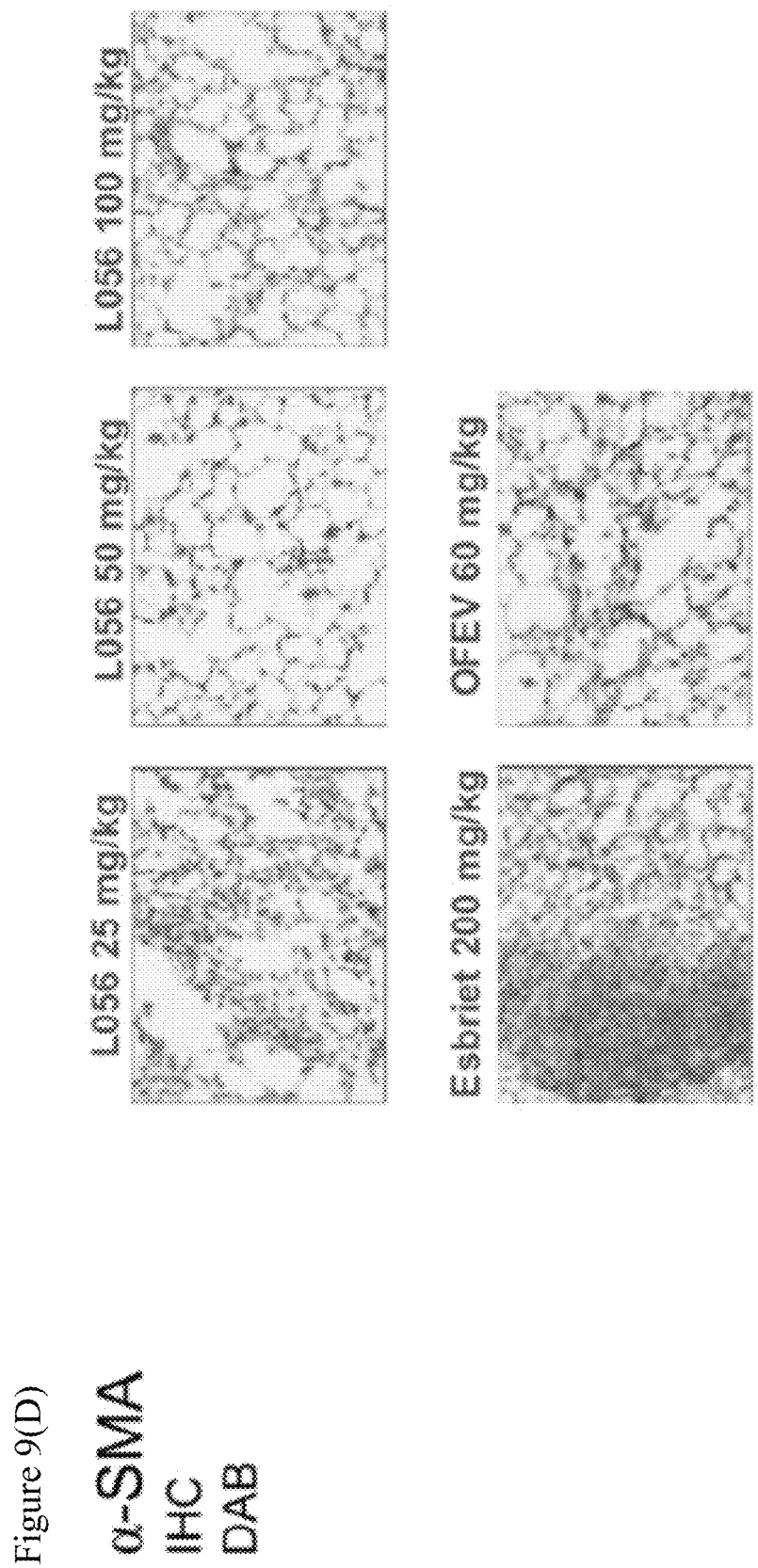
Figure 9(D) α-SMA IHC DAB

AMINONAPHTHOQUINONE COMPOUNDS FOR TREATMENT AND/OR PREVENTION OF FIBROSIS DISEASES

CROSS-REFERENCE TO RELATED APPLICATIONS

This application is a § 371 national stage entry of International Application No. PCT/US2016/062568, filed Nov. 17, 2016, which claims the benefit of U.S. Provisional Application No. 62/256,516, filed Nov. 17, 2015, the entire contents of which are incorporated herein by reference.

FIELD OF THE INVENTION

The invention relates to a method or use for treating and/or preventing fibrosis disease. Particularly, the method uses aminonaphthoquinone compounds to treat and/or prevent fibrosis diseases.

BACKGROUND OF THE INVENTION

Normal tissue repair processes are critical for maintaining proper tissue function. Fibrosis is an excessive growth of fibrous connective tissue in an organ, any part, or tissue thereof, for example in a liver, any part or tissue thereof, especially in response to an injury. Fibrosis affects many organ systems, including the lung, kidney, liver and heart; and many disease processes, including cardiomyopathies, hypertension, chronic hepatitis C infection, adult respiratory distress syndrome, and sarcoidosis are accompanied by fibrosis. For example, hepatic fibrosis is overly exuberant wound healing in which excessive connective tissue builds up in the liver. Chronic liver diseases can lead to liver fibrosis with the principle causes chronic viral hepatitis B and alcoholic liver disease. Pulmonary fibrosis (literally "scarring of the lungs") is a respiratory disease in which scars are formed in the lung tissues, leading to serious breathing problems. Scar formation, the accumulation of excess fibrous connective tissue (the process called fibrosis), leads to thickening of the walls, and causes reduced oxygen supply in the blood. As a consequence patients suffer from perpetual shortness of breath. Renal fibrosis is the inevitable consequence of an excessive accumulation of extracellular matrix that occurs in virtually every type of chronic kidney disease. Intestinal fibrosis is a common complication of inflammatory bowel disease (IBD) and can occur in both ulcerative colitis (UC) and Crohn's disease (CD), but is much more prevalent in CD. Fibrosis can also occur in the heart, e.g., cardiac fibrosis can occur as a thickening of a heart valve. Current therapies to treat fibrotic conditions, including dermal fibrosis and liver fibrosis, have a limited efficacy.

Proteasomes play a major role in the degradation of many proteins that are involved in cell cycling, proliferation, and apoptosis. They have at least three distinct endopeptidase activities which include hydrolysis of peptide bonds on the carboxyl side of hydrophobic, basic, and acidic amino acid residues. Proteasomes, through their protein degradation activity, have been implicated in several important cell functions, including DNA repair, cell cycle progression, signal transduction, transcription, and antigen presentation. Proteasome inhibition represents an important new strategy in cancer treatment. U.S. Pat. Nos. 7,442,830, 8,003,819 and 8,058,262 relate to boronic acid and boronic ester compounds useful as proteasome inhibitors. U.S. Pat. No. 8,389,564 provides salinosporamide used to treating and/or ameliorating a disease or condition, such as cancer, a microbial disease and/or inflammation. WO 2010/005534 provides compounds having activity as inhibitors of proteasomes.

However, there are no reports showing that proteasome inhibitors are related to fibrosis diseases.

SUMMARY OF THE INVENTION

The invention provides a method for prevention and/or treatment of a fibrosis disease in a subject, comprising administering an effective amount of a compound of Formula (I) described herein or a pharmaceutically acceptable salt, solvate or prodrug as an active ingredient to the subject. Preferably, the effective amount is in a range of about 1.5 mg/kg/day to about 20 mg/kg/day to the subject. In some embodiments, the effective amount of the active ingredient ranges from about 1.5 mg/kg/day to about 15 mg/kg/day, about 1.5 mg/kg/day to about 13 mg/kg/day, about 1.5 mg/kg/day to about 12 mg/kg/day, about 1.5 mg/kg/day to about 10 mg/kg/day, about 2.0 mg/kg/day to about 20 mg/kg/day, about 2.0 mg/kg/day to about 15 mg/kg/day, about 2.0 mg/kg/day to about 13 mg/kg/day or about 2.0 mg/kg/day to about 12 mg/kg/day, about 5 mg/kg/day to about 20 mg/kg/day, about 5 mg/kg/day to about 15 mg/kg/day or about 5 mg/kg/day to about 10 mg/kg/day. In some embodiments, the active ingredient of the method of the invention is further co-administered with a second anti-fibrosis agent. Preferably, the second anti-fibrosis agent is ESBRIET (pirfenidone), OFEV (nintedanib), LOXL2 antibody (such as simtuzumab), IL-13 antibody (lebrikizumab), αVβ6 antibody (such as STX-100), CTGF antibody (such as FG-3019), tipelukast (such as MN-001) or aerosol pirfenidone (such as GP-101). In some embodiments, the fibrosis disease is skin fibrosis, lung fibrosis, renal fibrosis, liver fibrosis, intestinal fibrosis, cystic fibrosis, cardiac fibrosis, uterine leiomyoma or adenomyosis. In a further embodiment, the lung fibrosis is idiopathic pulmonary fibrosis.

The invention also provides a pharmaceutical composition comprising a compound of Formula (I) or a pharmaceutically acceptable salt, solvate or prodrug as an active ingredient in one or more unit dosage forms. Preferably, the dosage form is in one or more capsule forms or tablet forms.

BRIEF DESCRIPTION OF THE DRAWING

FIG. 1(A), Western blot plot; FIG. 1(B), Quantitative assay of Western blot.

FIG. 2(A), Western blot plot; FIG. 2(B), Quantitative assay of Western blot.

FIG. 3(A), Western blot plot; FIG. 3(B), Quantitative assay of Western blot.

FIG. 4(A), Western blot plot; FIG. 4(B), Quantitative assay of Western blot; FIG. 4(C), Immunofluorescence plot.

FIG. 5(A), Western blot plot; FIG. 5(B), Quantitative assay of Western blot.

FIG. 6(A), Western blot plot; FIG. 6(B), Quantitative assay of Western blot; FIG. 6(C), Immunofluorescence plot.

FIG. 8(A), Histology fibrosis score plot; FIG. 8(B), H&E staining plot.

FIGS. 9(A) to 9(D) show the inhibitory effects on pro-fibrogenic mediators, collagen, CTGF, fibronectin and α-SMA, respectively. FIG. 9(A), H&E staining plot for collagen; FIG. 9(B), H&E staining plot for CTGF; FIG. 9(C), H&E staining plot for fibronectin; FIG. 9(D), H&E staining plot for α-SMA.

FIG. 10(A) sinus red stain; FIG. 10(B), the inhibition of MPT0L056 on CC14-induced liver fibrosis.

DETAILED DESCRIPTION OF THE INVENTION

Figure 1A:
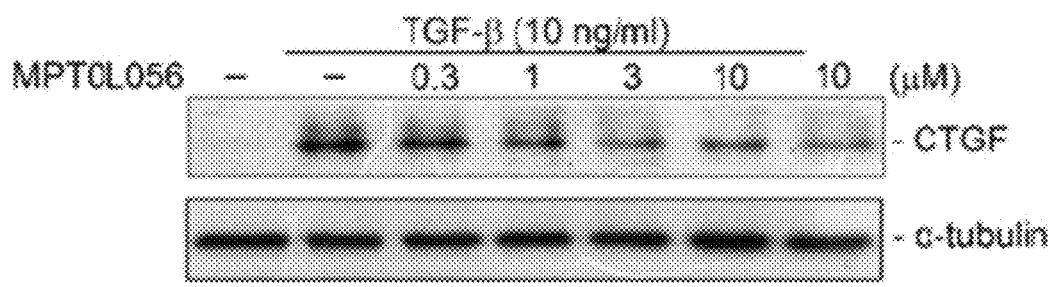
FIGS. 1(A) and 1(B) show the effects of L056 on TGF-β-induced CTGF expression in WI-38 cells. WI-38 lung fibroblasts were incubated with different concentrations of L056 (0.3, 1, 3 or 10 µM) for 30 min before and during incubation for 2 h with TGF-β (10 ng/mL). L056 significantly inhibited TGF-β-induced CTGF production from WI-38 lung fibroblasts in a concentration-dependent manner.

The invention is, at least in part, based on the discovery of using aminonaphthoquinone compounds and their effective dose in the prevention and/or treatment of fibrosis diseases. Particularly, the compounds can effectively prevent and/or treat a fibrosis disease without cytotoxicity or genotoxicity.

As used herein, except where the context requires otherwise, the term "comprise" and variations of the term, such as "comprising," "comprises" and "comprised" are not intended to exclude other additives, components, integers or steps.

As used herein, except where the context requires otherwise, the method steps disclosed are not intended to be limiting nor are they intended to indicate that each step is essential to the method or that each step must occur in the order disclosed.

As used herein, the use of "or" means "and/or" unless stated otherwise. In the context of a multiple dependent claim, the use of "or" refers back to more than one preceding independent or dependent claim in the alternative only.

As used herein, all numbers are approximate, and may be varied to account for measurement error and the rounding of significant digits. The use of "about" before certain measured quantities includes variations due to sample impurities, measurement error, human error, and statistical variation, as well as the rounding of significant digits.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal and ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "prodrug" refers to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides.

The terms "administer," "administering," or "administration," as used herein, refers to implanting, absorbing, ingesting, injecting, inhaling, or otherwise introducing an inventive compound, or a pharmaceutical composition thereof, in or on a subject.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "pharmaceutically acceptable carrier" refers to a solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. Pharmaceutically acceptable carriers are determined in part by the particular composition being administered, as well as by the particular method used to administer the composition.

As used herein, the term "subject" is defined herein to include animals such as mammals, including, but not limited to, primates (e.g., humans), cows, sheep, goats, horses, dogs, cats, rabbits, rats, mice and the like. In specific embodiments, the subject is a human. The terms "subject" and "patient" are used interchangeably herein in reference, for example, to a mammalian subject, such as a human.

As used herein, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agents, after the diagnosis or onset of symptoms of the particular disease.

As used herein, the terms "prevent," "preventing" and "prevention" refer to the prevention of the onset, recurrence or spread of a disease or disorder, or of one or more symptoms thereof. In certain embodiments, the terms refer to the treatment with or administration of a compound or an antibody or dosage form provided herein, with or without one or more other additional active agents, prior to the onset of symptoms, particularly to patients at risk of disease or disorders provided herein. The terms encompass the inhibition or reduction of a symptom of the particular disease. In this regard, the term "prevention" may be interchangeably used with the term "prophylactic treatment."

As used herein, the terms "co-administration" and "in combination with" include the administration of two or more therapeutic agents simultaneously, concurrently, separately or sequentially within no specific time limits unless otherwise indicated. In one embodiment, the therapeutic agents are in the same composition or unit dosage form. In other embodiments, the therapeutic agents are in separate compositions or unit dosage forms.

In one aspect, the invention provides a method for prevention and/or treatment of a fibrosis disease in a subject, comprising administering an effective amount of a compound with the following general Formula (I) or an isomer, a stereoisomer, a pharmaceutically acceptable salt, solvate or prodrug thereof as an active ingredient to a subject,

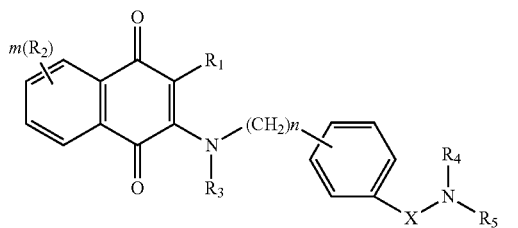

wherein
- $R_1$ is halogen, $C_{1-10}$alkyl, $C_{2-10}$alkenyl, $C_{2-10}$alkynyl, $NH_2$, $NO_2$, OH or CN; each $R_2$ is the same or different, representing H, $C_{1-10}$alkyl, $C_{2-10}$alkenyl, $C_{2-10}$alkynyl, $NH_2$, $NO_2$, $C_{1-10}$alkyloxy, $C_{1-10}$alkylthio, $C_{1-10}$alkylamino, $C_{1-10}$alkyloxy$C_{1-10}$alkyl, OH or CN, $C_{6-10}$aryl or $C_{5-7}$heterocyclic having 1 to 3 heteroatoms selected from the group consisting of N, O and S;
- $R_3$ is H, $C_{1-10}$alkyl, $C_{2-10}$alkenyl, $C_{2-10}$alkynyl, $NH_2$, $NO_2$, OH or CN;
- $R_4$ is H, $C_{1-10}$alkyl, $C_{2-10}$alkenyl, $C_{2-10}$alkynyl, $NH_2$, $NO_2$, OH or CN, or $R_4$ together with nitrogen atom attached therefrom and $R_5$ form a fused bicyclic ring having 0 to 3 heteroatoms selected from O; N and S;
- $R_5$ is absent, OH, $C_{3-10}$cycloalkyl, $C_{6-10}$aryl, $C_{5-7}$heterocyclic ring having 0 to 3 heteroatoms selected from O; N and S or $C_{10-12}$ fused heterocyclic ring having 0 to 3 heteroatoms selected from O; N and S, each of cycloalkyl, aryl, heterocyclic ring and fused heterocyclic ring is unsubstituted or substituted with one to three of OH; halogen; $NH_2$; $NO_2$, CN, $C_{1-10}$alkyl; $C_{2-10}$alkenyl; $C_{2-10}$alkynyl; $C_{1-10}$alkyloxy; $C_{5-10}$heteroaryl having 1 to 3 heteroatoms selected from the group consisting of N, O and S, unsubstituted or substituted with $C_{1-10}$alkyl, $C_{2-10}$alkenyl, $C_{2-10}$alkynyl, OH, halogen, CN, $NH_2$ or $NO_2$; —S(O)$_2$-phenyl wherein the phenyl is unsubstituted or substituted with halogen, OH, CN, $NH_2$, $NO_2$, $C_{1-10}$alkyl, $C_{2-10}$alkenyl, $C_{2-10}$alkynyl or $C_{1-10}$alkyloxy; —C(O)NHOH; —C(O)NH$_2$; —C(O)-phenyl wherein phenyl is unsubstituted or substituted with 1-5 same or different substituents selected from the group consisting of OH, halogen, CN, $NH_2$, $NO_2$, $C_{1-10}$alkyl, $C_{2-10}$alkenyl, $C_{2-10}$alkynyl or $C_{1-10}$alkyloxy; —C(O)$NR_aR_b$; NHS(O)$_2$phenyl wherein phenyl is optionally substituted with OH, halogen, CN, $NH_2$, $NO_2$, $C_{1-10}$alkyl, $C_{2-10}$alkenyl, $C_{2-10}$alkynyl or $C_{1-10}$alkyloxy; $C_{1-10}$alkylene-heteroaryl; —S(O)$_2$-heteroaryl; —S(O)$_2$-heterocyclic ring; —S(O)$_2$N(H)-heteroaryl; -alkylene-N(H)-heteroaryl; heterocylic ring unsubstituted or substituted with $C_{1-10}$alkyl; or
- $R_5$ is alkylene-$R_6$ wherein $R_6$ is OH, $NO_2$, CN, alkyl, alkenyl, alkynyl, $NR_aR_b$, cycloalkyl, aryl, heterocyclic ring having 0 to 3 heteroatoms selected from O; N and S or fused heterocyclic ring having 0 to 3 hetero atoms selected from O, N and S, each of cycloalkyl, aryl, heterocyclic ring and fused heterocyclic ring is unsubstituted or substituted with one to three of OH; halogen; $NH_2$; $NO_2$, CN, alkyl; alkenyl; alkynyl; alkyloxy; heteroaryl having 1 to 3 heteroatoms selected from the group consisting of N, O and S, unsubstituted or substituted with alkyl, alkenyl, alkynyl, OH, halogen, CN, $NH_2$ or $NO_2$; and
- $R_a$ and $R_b$, are the same or different, independently representing H; OH; alkyl; alkenyl; alkynyl; alkyloxy; cycloalkyl; heterocylyl; alkyleneamino; alkylene-N-(alkyl)$_2$; aryl unsubstituted or substituted with OH, halogen, CN, $NH_2$, $NO_2$, alkyl, alkenyl, alkynyl, alkyloxy or heteroaryl; heteroaryl unsubstituted or substituted with OH, halogen, CN, $NH_2$, $NO_2$, alkyl, alkenyl, alkynyl or alkyloxy; alkylene-heteroaryl; or alkyleneheterocylyl unsubstituted or substituted with alkyl;
- X is —C(O), —S(O)$_2$ or —NH—C(O)—;
- Y is —C— or —N—;
- m is an integer of 0-3; and
- n is an integer of 0-7.

In another aspect, the invention provides a compound with the general Formula (I) described herein or an isomer, a stereoisomer, a pharmaceutically acceptable salt, solvate or prodrug thereof for prevention and/or treatment of a fibrosis disease in a subject. Alternatively, the invention provides a use of a compound with the general Formula (I) described herein or an isomer, a stereoisomer, a pharmaceutically acceptable salt, solvate or prodrug thereof for the manufacture of a medicament for prevention and/or treatment of a fibrosis disease in a subject.

In some embodiments of formula (I), m is 0; $R_1$ is halogen; n is any integer of 1-4; $R_3$ is H; X is —C(O)—; $R_4$ is H; and $R_5$ is OH; $C_{3-8}$cycloalkyl; phenyl unsubstituted or substituted with one to three same or different substituents selected from OH, CN, halogen, $NH_2$ or $C_{1-4}$alkylpiperazinyl; $C_{1-6}$alkylpiperazinyl; $C_{1-6}$alkylpyridinyl; $C_{1-6}$alkylpyrrolidinyl; pyridinyl; pyrimidinyl; pyrazinyl; piperazinyl; pyrrolidinyl; thiazolyl; benzimidazolyl; pyrazolyl; indazolyl; pyrazolyl; quinolinyl; indolyl; $C_{1-4}$indolyl; indazolyl; azaindolyl; azaindazolyl; deazapurinyl; indanyl; morpholinoyl or $C_{1-4}$alkylmorpholinoyl, each of which is unsubstituted or substituted with one, two or three groups selected from OH, CN, halogen or $NH_2$.

In some embodiments of formula (I), m is 0; $R_1$ is halogen; n is any integer of 1-2; $R_3$ is H; X is —C(O); $R_4$ is H; and $R_5$ is OH; $C_{3-8}$cycloalkyl; pyridinyl; phenyl substituted by one to three of $NH_2$, halogen, OH, CN or $C_{1-4}$alkylpiperazinyl; pyrinidinyl unsubstituted or substituted $NO_2$, $NH_2$ or $C_{1-4}$alkyl; pyrazinyl unsubstituted or substituted $NO_2$, $NH_2$ or $C_{1-4}$alkyl; thiazolyl unsubstituted or substituted $NO_2$, $NH_2$ or $C_{1-4}$alkyl; benzimidazolyl unsubstituted or substituted $NO_2$, $NH_2$ or $C_{1-4}$alkyl; pyrazolyl unsubstituted or substituted $NO_2$, $NH_2$ or $C_{1-4}$alkyl; indazolyl unsubstituted or substituted $NO_2$, $NH_2$ or $C_{1-4}$alkyl; thiazolyl unsubstituted or substituted $NO_2$, $NH_2$ or $C_{1-4}$alkyl; quinolinyl unsubstituted or substituted $NO_2$, $NH_2$ or $C_{1-4}$alkyl; indolyl unsubstituted or substituted $NO_2$, $NH_2$ or $C_{1-4}$alkyl; indazolyl unsubstituted or substituted $NO_2$, $NH_2$ or $C_{1-4}$alkyl; azaindolyl unsubstituted or substituted $NO_2$, $NH_2$ or $C_{1-4}$alkyl; deazapurinyl unsubstituted or substituted $NO_2$, $NH_2$ or $C_{1-4}$alkyl; indanyl unsubstituted or substituted $NO_2$, $NH_2$ or $C_{1-4}$alkyl; or morpholinoyl unsubstituted or substituted $NO_2$, $NH_2$ or $C_{1-4}$alkyl.

In some embodiments of formula (I), m is 0; n is 0; X is —C(O); Y is —N—; $R_1$ is halogen or $C_{1-4}$alkyl; $R_3$ is H; $R_4$ is H or $C_{1-4}$alkyl; and $R_5$ is pyridinyl, pyrazinyl, or pyrimidinyl.

In some embodiments of formula (I), m is 0; n is 0; X is —C(O); Y is —N—; $R_1$ is halogen; $R_3$ is H; $R_4$ is H; and $R_5$ is pyridinyl, pyrazinyl, or pyrimidinyl.

In some embodiments of formula (I), m is 0; n is 0; X is S(O)$_2$; Y is —N—; $R_1$ is halogen or $C_{1-4}$alkyl; $R_3$ is H; and $R_4$ together with nitrogen atom attached therefrom and $R_5$ form a fused bicyclic ring. Preferably, the fused bicyclic ring is indolyl or azaindolyl.

In some embodiments of formula (I), m is 0; $R_1$ is halogen; n is any integer of 1-4; $R_3$ is H; X is C(O); $R_4$ is H;

$R_5$ is alkylene-$R_6$ wherein $R_6$ is $NR_aR_b$, $C_{5-7}$heterocyclic ring having 0 to 3 hetero atoms selected from O, N and S; or $C_{10-12}$ fused heterocyclic ring having 0 to 3 hetero atoms selected from O, N and S; and $R_a$ and $R_b$ are alkyl.

In some embodiments of formula (I), m is 0; $R_1$ is halogen; n is any integer of 1-2; $R_3$ is H; X is C(O); $R_4$ is H; $R_5$ is $(CH_2)_{1-4}R_6$ wherein $R_6$ is unsubstituted or substituted pyrrolidinyl, oxolanyl, thiolanyl, pyrrolyl, furanyl, thiophenyl, piperidinyl, oxanyl, thianyl, morpholinoyl, pyridinyl, piperidinyl, piperazinyl, thiopyranyl, pyrazinyl, pyrimidinyl, pyridazinyl, thiazolyl; benzimidazolyl; pyrazolyl; indazolyl; pyrazolyl; quinolinyl; indolyl; indazolyl; azaindolyl; azaindazolyl; deazapurinyl; or indanyl.

In some embodiments of formula (I), m is 0; $R_1$ is halogen; n is any integer of 1-2; $R_3$ is H; X is C(O); $R_4$ is H; $R_5$ is $(CH_2)_{1-4}R_6$ wherein $R_6$ is unsubstituted or substituted pyrrolidinyl, morpholinoyl, pyridinyl, piperidinyl, piperazinyl, or indolyl.

In some embodiments of formula (I), the compounds include but are not limited to the following:

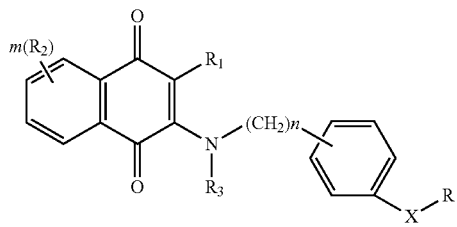

m is 0; $R_3$ is H; X is C(O); and R is

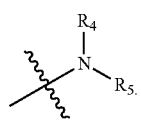

| Example (Compound #) | Code | Number | $R_1$ | $(CH_2)_n$ | R | Structure of R |
|---|---|---|---|---|---|---|
| Example 1 (1) | MPT0L016 | 19-1304 | Cl | $CH_2$ | NHOH | |
| Example 2 (2) | MPT0L018 | 19-1312 | Cl | $CH_2$ | 2-aminopyridine | |
| Example 3 (3) | MPT0L019 | 19-1313 | Cl | $CH_2$ | 2-aminobenzamide | |
| Example 4 (4) | MPT0L055 | 31-324 | Cl | $CH_2$ | 3-aminopyridine | |
| Example 5 (5) | MPT01056 | 31-326 | Cl | $CH_2$ | 4-aminopyridine | |
| Example 39 (6) | MPT0L080 | 19-1637 | Br | $CH_2$ | 2-aminopyridine | |
| Example 42 (7) | MPT0L101 | 31-482 | Cl | $CH_2$ | 4-aminopyrimidine | |
| Example 43 (8) | MPT0L076 | 31-396 | Cl | $CH_2$ | 2-aminopyrazine | |

-continued

| Example (Compound #) | Code | Number | R₁ | (CH₂)ₙ | R | Structure of R |
|---|---|---|---|---|---|---|
| Example 6 (9) | MPT0L081 | 19-1652 | Cl | CH₂ | 3-fluoroaniline | |
| Example 7 (10) | MPT0L082 | 19-1653 | Cl | CH₂ | 4-fluoroaniline | |
| Example 8 (11) | MPT0L083 | 19-1654 | Cl | CH₂ | Aniline | |
| Example 9 (12) | MPT0L084 | 19-1655 | Cl | CH₂ | 2-fluoroaniline | |
| Example 10 (13) | MPT0L085 | 19-1658B | Cl | CH₂ | 2-aminothiazole | |
| Example 11 (14) | MPT0L086 | 19-1659 | Cl | CH₂ | 2-aminobenzimidazole | |
| Example 12 (15) | MPT0L087 | 19-1666 | Cl | CH₂ | 4-aminophenol | |
| Example 13 (16) | MPT0L088 | 19-1673 | Cl | CH₂ | 3-ethynylaniline | |
| Example 14 (17) | MPT0L092 | 19-1678A | Cl | CH₂ | 2-fluoro-4-iodoaniline | |
| Example 15 (18) | MPT0L093 | 19-1703 | Cl | CH₂ | 5-aminobenzimidazole | |
| Example 16 (19) | MPT0L094 | 19-1704 | Cl | CH₂ | (N1-)3-aminopyrazole | |

-continued

| Example (Compound #) | Code | Number | R₁ | (CH₂)ₙ | R | Structure of R |
|---|---|---|---|---|---|---|
| Example 17 (20) | MPT0L095 | 19-1705 | Cl | CH₂ | Cyclopropylamine | 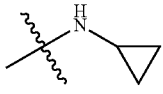 [SMILES: *NC1CC1] |
| Example 18 (21) | MPT0L096 | 19-1706 | Cl | CH₂ | Cyclopentylamine | 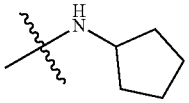 [SMILES: *NC1CCCC1] |
| Example 19 (22) | MPT0L097 | 19-1708 | Cl | CH₂ | 5-aminoindazole | 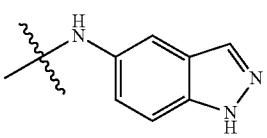 [SMILES: *Nc1ccc2[nH]ncc2c1] |
| Example 20 (23) | MPT0L098 | 19-1709 | Cl | CH₂ | 2-amino-5-methylthiazole | 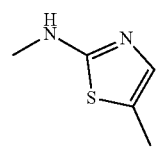 |
| Example 21 (24) | MPT0L099 | 19-1712A-2 | Cl | CH₂ | 3-amino-5-methylpyrazole | 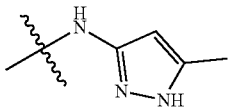 [SMILES: *Nc1cc(C)[nH]n1] |
| Example 22 (25) | MPT0L100 | 19-1712B | Cl | CH₂ | (N1-)3-amino-5-methylpyrazole | 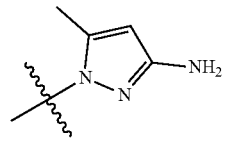 [SMILES: *n1nc(N)cc1C] |
| Example 23 (26) | MPT0L103 | 19-1716B | Cl | CH₂ | 4-amino-3-nitropyridine | 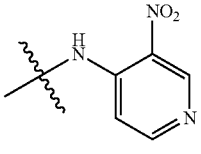 |
| Example 24 (28) | MPT0L108 | 19-1830-2 | Cl | CH₂ | 6-aminoquinoline | 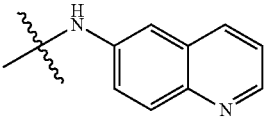 [SMILES: *Nc1ccc2ncccc2c1] |
| Example 25 (29) | MPT0L109 | 19-1831 | Cl | CH₂ | 8-aminoquinoline | 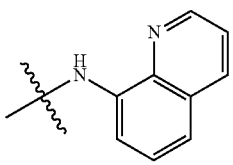 [SMILES: *Nc1cccc2cccnc12] |
| Example 26 (30) | MPT0L110 | 19-1834 | Cl | CH₂ | 3-aminoquinoline | 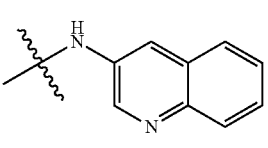 [SMILES: *Nc1cnc2ccccc2c1] |
| Example 27 (31) | MPT0L111 | 19-1835 | Cl | CH₂ | 5-aminoquinoline | 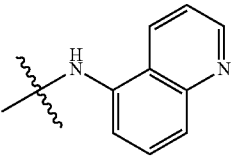 [SMILES: *Nc1cccc2ncccc12] |

-continued

| Example (Compound #) | Code | Number | R₁ | (CH₂)ₙ | R | Structure of R |
|---|---|---|---|---|---|---|
| Example 28 (32) | MPT0L112 | 19-1854-2 | Cl | CH₂ | 4-amino-2-methylquinoline | |
| Example 29 (33) | MPT0L113 | 19-1858-2 | Cl | CH₂ | 5-aminoindole | |
| Example 30 (34) | MPT0L114 | 19-1859B | Cl | CH₂ | 5-amino-2-methylindole | |
| Example 31 (35) | MPT0L115 | 19-1867 | Cl | CH₂ | 7-aminoindole | |
| Example 32 (36) | MPT0L116 | 19-1875 | Cl | CH₂ | 4-aminoindole | |
| Example 33 (37) | MPT0L117 | 19-1879 | Cl | CH₂ | 4-(N-ethylpiperazine)aniline | |
| Example 34 (38) | MPT0L118 | 19-1887 | Cl | CH₂ | 6-aminoindazole | |
| Example 35 (39) | MPT0L119 | 19-1890 | Cl | CH₂ | 5-amino-7-azaindole | |
| Example 36 (40) | MPT0L120 | 19-1891 | Cl | CH₂ | 5-amino-7-azaindazole | |
| Example 37 (41) | MPT0L121 | 19-1898A | Cl | CH₂ | 6-amino-N1-methyl-7-deazapurine | |

-continued

| Example (Compound #) | Code | Number | R₁ | (CH₂)ₙ | R | Structure of R |
|---|---|---|---|---|---|---|
| Example 38 (42) | MPT0L124 | 19-1903 | Cl | CH₂ | 4-aminoindan | |
| Example 44 (27) | MPT0L102 | 19-1717 | Cl | CH₂ | 4-aminomethylpyridine | |
| Example 45 (43) | MPT0L122 | 19-1935 | Cl | CH₂ | 2-morpholinoethanamine | |
| Example 46 (44) | MPT0L123 | 19-1936 | Cl | CH₂ | tryptamine | |
| Example 47 (45) | MPT0L132 | | Cl | CH₂ | N,N'-dimethylethanamine | |
| Example 48 (46) | MPT0L133 | | Cl | CH₂ | N-2-(pyrrolidin-1-yl)ethyl | |
| Example 49 (47) | MPT0L134 | | Cl | CH₂ | N,N'-diethylethanamine | |
| Example 50 (48) | MPT0L136 | | Cl | CH₂ | N-2-(piperidin-1-yl)ethyl | |
| Example 51 (49) | MPT0L137 | | Cl | CH₂ | N-2-(4-methylpiperazin-1-yl (ethyl | |

The compounds of the present invention can be prepared using methods known to those skilled in the art in view of this disclosure. The compounds and their preparation methods described herein are disclosed in PCT/US2015/041767 and U.S. Ser. No. 62/199,207. For example, the preferred compounds of the invention can be prepared as shown in the following schemes:

Scheme 1

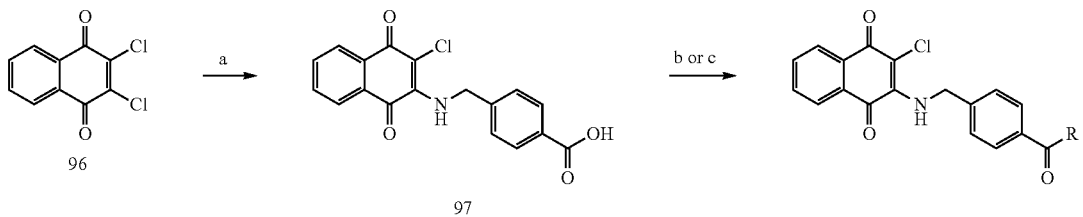

1 R = NHOH
2 R = 2-aminopyridine
3 R = 2-aminobenzamide
4 R = 3-aminopyridine
5 R = 4-aminopyridine
9 R = 3-fluoroaniline
10 R = 4-fluoroaniline
11 R = aniline
12 R = 2-fluoroaniline
13 R = 2-aminothiazole
14 R = 2-aminobenzimidazole
15 R = 4-aminophenol
16 R = 3-ethynylaniline
17 R = 2-fluoro-4-iodoaniline
18 R = 5-aminobenzimidazole
19 R = (N1)-3-aminopyrazole
20 R = cyclopropylamine
21 R = cyclopentylamine
22 R = 5-aminoindazole
23 R = 2-amino-5-methylthiazole
24 R = 3-amino-5-methylpyrazole
25 R = (N1)-3-amino-5-methylpyrazole
26 R = 4-amino-3-nitropyridine
28 R = 6-aminoquinoline
29 R = 8-aminoquinoline
30 R = 3-aminoquinoline
31 R = 5-aminoquinoline
32 R = 4-amino-2-methylquinoline
33 R = 5-aminoindole
34 R = 5-amino-2-methylindole
35 R = 7-aminoindole
36 R = 4-aminoindole
37 R = 4-(N-ethylpiperazine)aniline
38 R = 6-aminoindazole
39 R = 5-amino-7-azaindole
40 R = 5-amino-7-azaindazole
41 R = 6-amino-N1-methyl-7-deazapurine
42 R = 4-aminoindan

*Reagents and condition
(a) 4-aminomethylbenzoic acid, TEA, EtOH, reflux
(b) EDC, HCl, HOBt, NMM, DMF, NH$_2$OTHP, r.t. then 10% TFA(aq.), MeOH, r.t. for 1
(c) substituted amine, HBTU, DIPEA, DMF, r.t. for 2-5, 9-44

Scheme 2

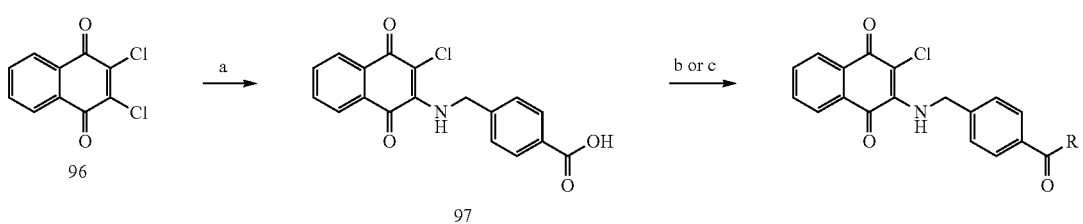

27 R = 4-aminomethylpyridine
43 R = 2-morpholinoethanamine
44 R = tryptamine
45 R = N,N'-dimethylethanamine
46 R = N-2-(pyrrolidin-1 yl)ethyl
47 R = N,N'-diethylethanamine
48 R = N-2-(piperidin-1 yl)ethyl
49 R = N-2-(4-methylpiperazin-1-yl)ethyl

*Reagents and condition
(a) 4-aminomethylbenzoic acid, TEA, EtOH, reflux
(b) substituted amine, HBTU, DIPEA, DMF, r.t. for 27, 43, 44
(c) substituted amine, EDC, HCl, HOBt, NMM, DMF, r.t. for 45-49

In one embodiment, the effective amount is in a range of about 1.5 mg/kg/day to about 20 mg/kg/day. In another embodiment, the effective amount for a human is in a range of about 2.0 mg/kg/day to about 15 mg/kg/day. On the other hand, the invention also provides a use of an effective amount of a compound of Formula (I) or a pharmaceutically acceptable salt, solvate or prodrug as an active ingredient for the manufacture of a medicament for prevention and/or treatment of a fibrosis disease.

In some further embodiments, the effective amount of the active ingredient or an isomer, a stereoisomer, a pharmaceutically acceptable salt, solvate or prodrug thereof used in the invention ranges from about 1.5 mg/kg/day to about 15 mg/kg/day, about 1.5 mg/kg/day to about 13 mg/kg/day, about 1.5 mg/kg/day to about 12 mg/kg/day, about 1.5 mg/kg/day to about 10 mg/kg/day, about 2.0 mg/kg/day to about 20 mg/kg/day, about 2.0 mg/kg/day to about 15 mg/kg/day, about 2.0 mg/kg/day to about 13 mg/kg/day or about 2.0 mg/kg/day to about 12 mg/kg/day, about 5 mg/kg/day to about 20 mg/kg/day, about 5 mg/kg/day to about 15 mg/kg/day or about 5 mg/kg/day to about 10 mg/kg/day. In a further embodiment, the effective amount used in the invention is about 2.3 mg/kg/day to about 11 mg/kg/day.

In one embodiment, the active ingredient of the invention is further co-administered with a second anti-fibrosis agent. Preferably, the second anti-fibrosis agent is ESBRIET (pirfenidone), OFEV (nintedanib), LOXL2 antibody (such as simtuzumab), IL-13 antibody (lebrikizumab), αVβ6 antibody (such as STX-100), CTGF antibody (such as FG-3019), tipelukast (such as MN-001) or aerosol pirfenidone (such as GP-101). In a further embodiment, the co-administration is simultaneous, separate or sequential administration.

In some embodiments, the fibrosis disease is skin fibrosis, lung fibrosis, renal fibrosis, liver fibrosis, intestinal fibrosis, cystic fibrosis, cardiac fibrosis, uterine leiomyoma or adenomyosis. In a further embodiment, the lung fibrosis is idiopathic pulmonary fibrosis. In another further embodiment, the treatment of lung fibrosis further comprises a co-administered therapy with lung transplantation, hyperbaric oxygen therapy (HBOT) or pulmonary rehabilitation.

In another aspect, the invention provides a pharmaceutical composition comprising a compound of Formula (I) or a pharmaceutically acceptable salt, solvate or prodrug as an active ingredient in one or more unit dosage forms. Preferably, the dosage form is in one or more capsule forms or tablet forms. In one embodiment, the compound of Formula (I) is 4-(((3-chloro-1,4-dioxo-1,4-dihydronaphthalen-2-yl)amino)methyl)-N-(pyridin-4-yl)benzamide.

In some embodiments, the pharmaceutical composition of the invention is in one or more capsule forms or tablet forms. In a further embodiment, the pharmaceutical composition of the invention comprises about 100 mg to about 300 mg, about 150 mg to about 300 mg, about 150 mg to about 250 mg, about 200 mg to 250 mg, about 220 mg to about 280 mg, about 220 mg to about 250 mg or about 200 mg to about 220 mg of the active ingredient in a single tablet; preferably, about 200 mg or 220 mg in a single tablet. In another further embodiment, the pharmaceutical composition of the invention comprises about 100 mg to about 500 mg, about 150 mg to about 500 mg, about 180 mg to about 500 mg, about 200 mg to about 500 mg, about 150 mg to about 350 mg, about 150 mg to about 300 mg, about 200 mg to about 400 mg, about 200 mg to about 400 about 350 mg, about 200 mg to about 300 mg, about 250 mg to about 500 mg, about 250 mg to about 400 mg, about 250 mg to about 350 mg or about 250 mg to about 300 mg of the active ingredient in a single capsule; preferably, about 250 mg of the active ingredient in a single capsule.

In one embodiment, the pharmaceutical composition of the invention comprises a second anti-fibrosis agent. Preferably, the second anti-fibrosis agent is ESBRIET (pirfenidone), OFEV (nintedanib), LOXL2 antibody (such as simtuzumab), IL-13 antibody (lebrikizumab), αVβ6 antibody (such as STX-100), CTGF antibody (such as FG-3019), tipelukast (such as MN-001) or aerosol pirfenidone (such as GP-101).

While it may be possible for the compounds of the invention to be administered as the raw chemical, it is also possible to present them as a pharmaceutical formulation. Accordingly, the present invention provides a pharmaceutical formulation or composition comprising a compound or a pharmaceutically acceptable salt, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Formulations may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Remington: The Science and Practice of Pharmacy, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration, although the most suitable route may depend, for example, upon the condition and disorder of the recipient. Oral administration is a preferred route. The formulations may conveniently be presented in unit dosage form and may be prepared by any of the methods well known in the art of pharmacy. All methods include the step of bringing into association a compound of the present invention or a pharmaceutically acceptable salt, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds or compositions of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds or compositions of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

Dosage regimens can be adjusted to provide the optimum therapeutic response. For example, several divided dosages may be administered daily or the dosage may be proportionally reduced as indicated by the exigencies of the therapeutic situation.

It is especially advantageous to formulate the compounds in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labelled or accompanied by a label indicating the intended method of treatment.

It is understood that the examples described herein are merely illustrative of the present invention. Certain modifications of the articles and/or methods employed may be made and still achieve the objectives of the invention. Such modifications are contemplated as within the scope of the claimed invention.

EXAMPLE

Preparation Examples

Example 1 4-(((3-chloro-1,4-dioxo-1,4-dihydronaphthalen-2-yl)amino)methyl)-N-hydroxybenzamide (1)

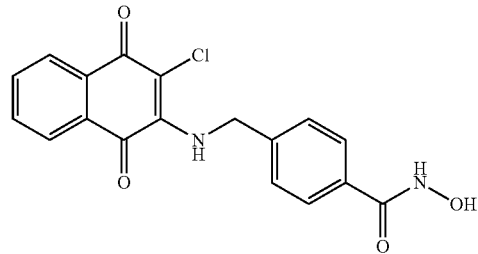 [SMILES: O=C(NO)c1ccc(CNC2=C(Cl)C(=O)c3ccccc3C2=O)cc1]

A mixture of 97 (0.36 g, 1.05 mmol), EDC.HCl (0.30 g, 1.58 mmol), HOBt (0.17 g, 1.26 mmol), NMM (0.28 ml, 2.52 mmol) and DMF (2.5 ml) was stirred for a while, to which was then added the o-(tetrahydro-2H-pyran-2-yl) hydroxylamine (0.15 g, 1.26 mmol) at room temperature, and the mixture was stirred overnight. The residue was purified by flash column over silica gel (ethyl acetate:n-hexane=2:1, Rf=0.45) to obtain the oily product. The oily product was then dissolved in MeOH (3 ml) and 10% TFA (aq.) (3 ml) added at room temperature and the mixture was stirred overnight. $H_2O$ was added to the reaction to produce the precipitant. The residue was filtered without further purification to afford 1 (0.24 g, 98.93%) as a red solid. $^1$H-NMR (500 MHz, DMSO-$d_6$): δ 4.98 (s, 2H), 7.35 (d, J=8.5 Hz, 2H), 7.68 (d, J=8.5 Hz, 2H), 7.73 (m, 1H), 7.81 (m, 1H), 7.96 (m, 2H), 8.03 (s, 1H).

Example 2 4-(((3-chloro-1,4-dioxo-1,4-dihydronaphthalen-2-yl)amino)methyl)-N-(pyridin-2-yl)benzamide (2)

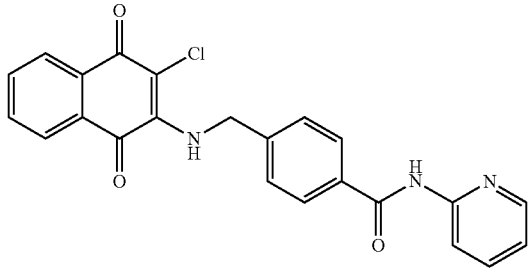 [SMILES: O=C(Nc1ccccn1)c1ccc(CNC2=C(Cl)C(=O)c3ccccc3C2=O)cc1]

A mixture of 97 (0.25 g, 0.73 mmol), EDC.HCl (0.21 g, 1.10 mmol), HOBt (0.12 g, 0.88 mmol), NMM (0.19 ml, 1.75 mmol) and DMF (2.0 ml) was stirred for a while, to which was then added 2-aminopyridine (0.08 g, 0.88 mmol) at room temperature and the mixture was stirred overnight. The residue was purified by flash column over silica gel (dichloromethane:methanol=30:1, Rf=0.50) to afford 2 (0.04 g, 13.11%) as a red solid. $^1$H-NMR (300 MHz, CDCl$_3$): δ 5.15 (d, J=6.6 Hz, 2H), 6.33 (s, 1H), 7.08-7.12 (m, 1H), 7.49 (d, J=8.4 Hz, 2H), 7.67 (m, 1H), 7.77 (m, 2H), 7.97 (d, J=8.4 Hz, 2H), 8.08 (m, 1H), 8.18 (m, 1H), 8.33 (m, 1H), 8.40 (d, J=8.4 Hz, 1H), 8.59 (br, 1H).

Example 3 N-(2-aminophenyl)-4-(((3-chloro-1,4-dioxo-1,4-dihydronaphthalen-2-yl)amino)methyl)benzamide (3)

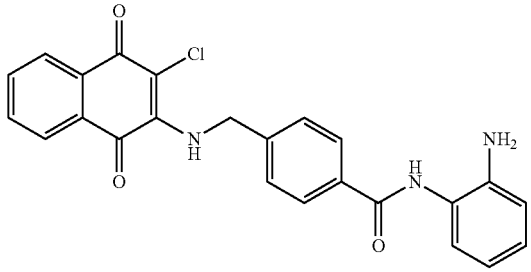 [SMILES: Nc1ccccc1NC(=O)c1ccc(CNC2=C(Cl)C(=O)c3ccccc3C2=O)cc1]

A mixture of 97 (0.25 g, 0.73 mmol), EDC.HCl (0.21 g, 1.10 mmol), HOBt (0.12 g, 0.88 mmol), NMM (0.19 ml, 1.75 mmol) and DMF (2.0 ml) was stirred for a while, to which was then added o-Phenylenediamine (0.08 g, 0.88 mmol) at room temperature and the mixture was stirred overnight. The residue was purified by flash column over silica gel (dichloromethane:methanol=30:1, Rf=0.50) to afford 3 (0.06 g, 19.03%) as a red solid. $^1$H-NMR (300 MHz, DMSO-d$_6$): δ 4.86 (s, 2H), 5.03 (s, 2H), 6.57 (t, J=7.8 Hz, 1H), 6.75 (d, J=6.6 Hz, 1H), 6.95 (t, J=7.8 Hz, 1H), 7.14 (d, J=6.6 Hz, 1H), 7.42 (d, J=7.8 Hz, 2H), 7.74 (t, J=7.2 Hz, 1H), 7.82 (t, J=7.2 Hz, 1H), 7.95 (m, 4H), 8.10 (br, 1H), 9.59 (s, 1H).

Example 4 4-(((3-chloro-1,4-dioxo-1,4-dihydronaphthalen-2-yl)amino)methyl)-N-(pyridin-3-yl)benzamide (4)

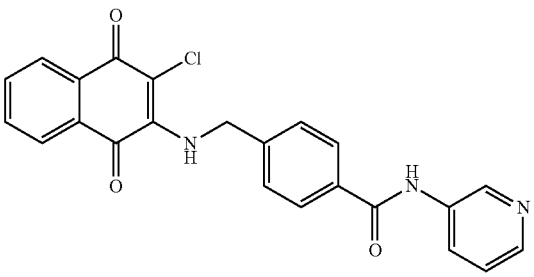 [SMILES: O=C(Nc1cccnc1)c1ccc(CNC2=C(Cl)C(=O)c3ccccc3C2=O)cc1]

A mixture of 97 (0.10 g, 0.29 mmol), HBTU (0.11 g, 0.29 mmol), DIPEA (0.06 ml, 0.35 mmol) and DMF (1.0 ml) was stirred for a while, to which was then added 3-aminopyridine (0.03 g, 0.35 mmol). The reaction was stirred for 16 h at room temperature. The residue was filtered without further purification to afford 4 (0.08 g, 66.02%). $^1$H NMR (300 MHz, DMSO-d$_6$): δ 5.03 (d, J=7.2 Hz, 2H), 7.37 (q, J=4.8 Hz, 1H), 7.46 (d, J=8.1 Hz, 2H), 7.74-7.82 (m, 2H), 7.91 (d, J=8.1 Hz, 2H), 7.95-7.98 (m, 2H), 8.13-8.17 (m, 2H), 8.27-8.29 (m, 1H), 10.42 (s, 1H).

Example 5 4-0(3-chloro-1,4-dioxo-1,4-dihydronaphthalen-2-yl)amino)methyl)-N-(pyridin-4-yl)benzamide (5)

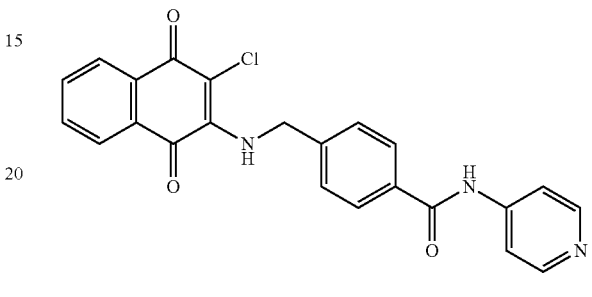

A mixture of 97 (0.10 g, 0.29 mmol), HBTU (0.11 g, 0.29 mmol), DIPEA (0.06 ml, 0.35 mmol) and DMF (1.0 ml) was stirred for a while, to which was then added 4-aminopyridine (0.03 g, 0.35 mmol). The reaction was stirred for 16 h at room temperature. The residue was filtered without further purification to afford 5 (0.08 g, 66.02%). $^1$H NMR (300 MHz, DMSO-d$_6$): δ 5.03 (d, J=7.2 Hz, 2H), 7.37 (d, J=8.4 Hz, 2H), 7.73-7.76 (m, 3H), 7.79-7.84 (m, 1H), 7.90 (d, J=8.4 Hz, 2H), 7.95-7.98 (m, 2H), 8.08-8.13 (m, 1H), 8.43-8.45 (m, 2H), 10.53 (s, 1H).

Example 6 4-(((3-chloro-1,4-dioxo-1,4-dihydronaphthalen-2-yl)amino)methyl)-N-(3-fluorophenyl)benzamide (9)

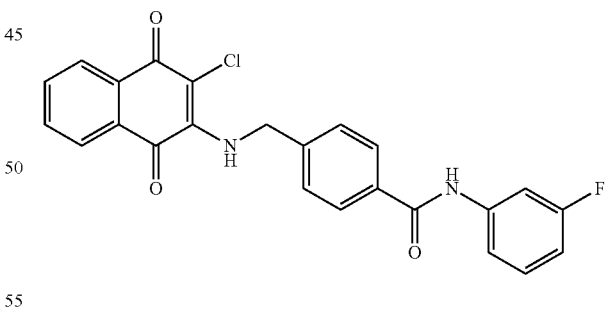

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-fluoroaniline (0.13 g, 1.32 mmol) at room temperature and the mixture was stirred overnight. The residue was purified by flash column over silica gel (ethyl acetate:n-hexane=1:2, Rf=0.30) to afford 9 (0.04 g, 10.45%) as a red solid. $^1$H-NMR (300 MHz, DMSO-d$_6$): δ 5.03 (s, 2H), 6.92 (m, 1H), 7.36 (m, 1H), 7.45 (d, J=8.1 Hz, 2H), 7.52 (m, 1H), 7.72 (m, 2H), 7.80 (m, 1H), 7.88 (d, J=8.4 Hz, 2H), 7.97 (m, 2H), 8.11 (br, 1H), 10.37 (s, 1H).

Example 7 4-(((3-chloro-1,4-dioxo-1,4-dihydronaphthalen-2-yl)amino)methyl)-N-(4-fluorophenyl)benzamide (10)

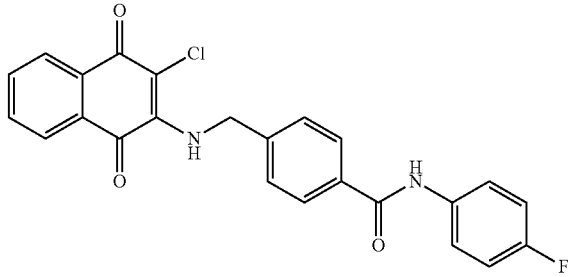 [SMILES: O=C(Nc1ccc(F)cc1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-fluoroaniline (0.13 g, 1.32 mmol) at room temperature and the mixture was stirred overnight. The residue was purified by flash column over silica gel (ethyl acetate:n-hexane=1:2, Rf=0.35) to afford 10 (0.02 g, 5.23%) as a red solid. $^1$H-NMR (300 MHz, DMSO-$d_6$): δ 5.02 (s, 2H), 7.16 (t, J=9.0 Hz, 2H), 7.43 (d, J=8.1 Hz, 2H), 7.75 (m, 3H), 7.82 (m, 1H), 7.88 (d, J=8.4 Hz, 2H), 7.97 (m, 2H), 8.08 (br, 1H), 10.24 (s, 1H).

Example 8 4-(((3-chloro-1,4-dioxo-1,4-dihydronaphthalen-2-yl)amino)methyl)-N-phenylbenzamide (11)

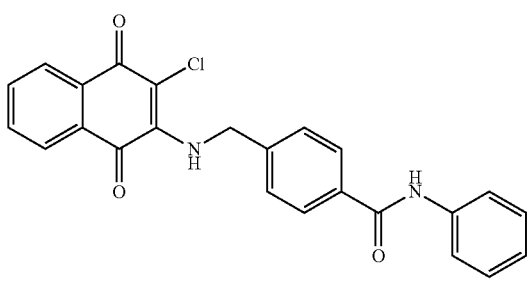 [SMILES: O=C(Nc1ccccc1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added aniline (0.12 g, 1.32 mmol) at room temperature and the mixture was stirred overnight. The residue was filtered by suction filtration to yield a red product. The residue was filtered without further purification to afford 11 (0.28 g, 76.33%) as a red solid. $^1$H-NMR (300 MHz, DMSO-$d_6$): δ 5.02 (s, 2H), 7.07 (t, J=7.5 Hz, 1H), 7.32 (d, J=7.5 Hz, 2H), 7.44 (d, J=8.4 Hz, 2H), 7.75 (m, 3H), 7.83 (m, 1H), 7.88 (d, J=8.4 Hz, 2H), 7.97 (m, 2H), 8.10 (br, 1H), 10.18 (s, 1H).

Example 9 4-(((3-chloro-1,4-dioxo-1,4-dihydronaphthalen-2-yl)amino)methyl)-N-(2-fluorophenyl)benzamide (12)

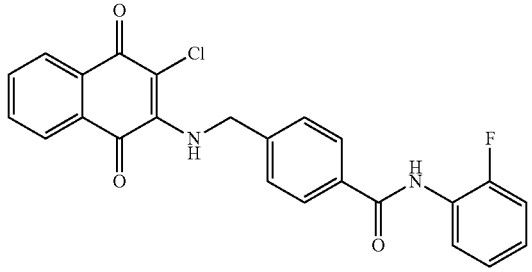 [SMILES: O=C(Nc1ccccc1F)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-fluoroaniline (0.13 g, 1.32 mmol) at room temperature and the mixture was stirred overnight. The residue was purified by flash column over silica gel (ethyl acetate:n-hexane=1:2, Rf=0.25) to afford 12 (0.02 g, 5.23%) as a red solid. $^1$H-NMR (300 MHz, DMSO-$d_6$): δ 5.03 (s, 2H), 7.23 (m, 3H), 7.44 (d, J=8.1 Hz, 2H), 7.56 (t, J=7.5 Hz, 1H), 7.74 (m, 1H), 7.80 (m, 1H), 7.91 (d, J=8.1 Hz, 2H), 7.97 (m, 2H), 8.10 (br, 1H), 10.05 (s, 1H).

Example 10 4-(((3-chloro-1,4-dioxo-1,4-dihydronaphthalen-2-yl)amino)methyl)-N-(thiazol-2-yl)benzamide (13)

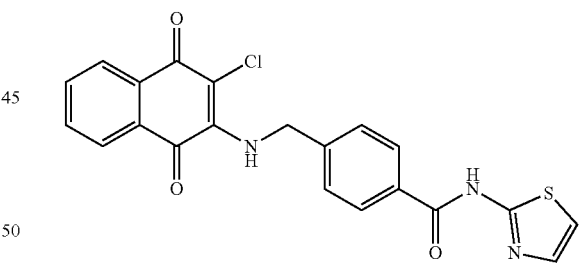

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-aminothiazole (0.13 g, 1.32 mmol) at room temperature and the mixture was stirred overnight. The residue was filtered by suction filtration to yield a red product. The residue was filtered without further purification to afford 13 (0.15 g, 40.21%) as a red solid. $^1$H-NMR (300 MHz, DMSO-$d_6$): δ 5.03 (d, J=7.2 Hz, 2H), 7.26 (d, J=3.6 Hz, 1H), 7.45 (d, J=8.4 Hz, 2H), 7.53 (d, J=3.6 Hz, 1H), 7.75 (m, 1H), 7.82 (m, 1H), 7.97 (m, 2H), 8.04 (d, J=8.4 Hz, 2H), 8.10 (t, J=7.5 Hz, 1H), 12.55 (s, 1H).

Example 11 N-(1H-benzo[d]imidazol-2-yl)-4-(((3-chloro-1,4-dioxo-1,4-dihydronaphthalen-2-yl)amino)methyl)benzamide (14)

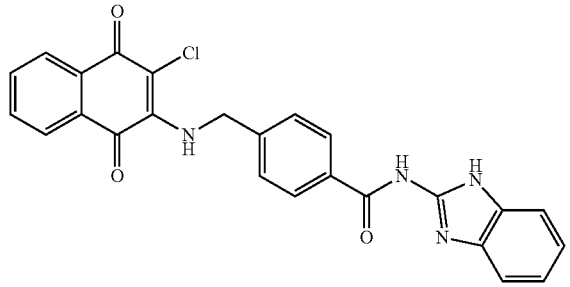 [SMILES: O=C(Nc1nc2ccccc2[nH]1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-aminobenzimidazole (0.18 g, 1.32 mmol) at room temperature and the mixture was stirred overnight. The residue was filtered by suction filtration to yield a red product. The residue was filtered without further purification to afford 14 (0.27 g, 67.16%) as a red solid. $^1$H-NMR (300 MHz, DMSO-$d_6$): δ 5.03 (d, J=6.9 Hz, 2H), 7.11 (m, 2H), 7.43 (d, J=9.0 Hz, 4H), 7.74 (m, 1H), 7.82 (m, 1H), 7.96 (d, J=5.7 Hz, 2H), 8.07 (d, J=8.4 Hz, 3H), 12.22 (s, 1H).

Example 12 4-(((3-chloro-1,4-dioxo-1,4-dihydronaphthalen-2-yl)amino)methyl)-N-(4-hydroxyphenyl)benzamide (15)

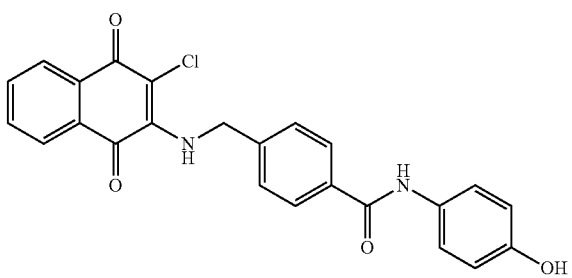 [SMILES: O=C(Nc1ccc(O)cc1)c1ccc(CNC2=C(Cl)C(=O)c3ccccc3C2=O)cc1]

A mixture of 97 (0.15 g, 0.44 mmol), HBTU (0.25 g, 0.66 mmol), DIPEA (0.11 ml, 0.66 mmol) and DMF (2.5 ml) was stirred for a while, to which was then added 4-aminophenol (0.07 g, 0.66 mmol) at room temperature and the mixture was stirred overnight. The residue was purified by flash column over silica gel (ethyl acetate:n-hexane=1:2, Rf=0.30) to afford 15 (0.02 g, 10.50%) as a brown solid. $^1$H-NMR (300 MHz, DMSO-$d_6$): δ 5.01 (d, J=6.3 Hz, 2H), 6.70 (d, J=9.0 Hz, 2H), 7.41 (d, J=8.4 Hz, 2H), 7.48 (d, J=8.7 Hz, 2H), 7.74 (m, 1H), 7.80 (m, 1H), 7.85 (d, J=8.4 Hz, 2H), 7.98 (m, 2H), 8.09 (br, 1H), 9.25 (br, 1H), 9.95 (s, 1H).

Example 13 4-(((3-chloro-1,4-dioxo-1,4-dihydronaphthalen-2-yl)amino)methyl)-N-(3-ethynylphenyl)benzamide (16)

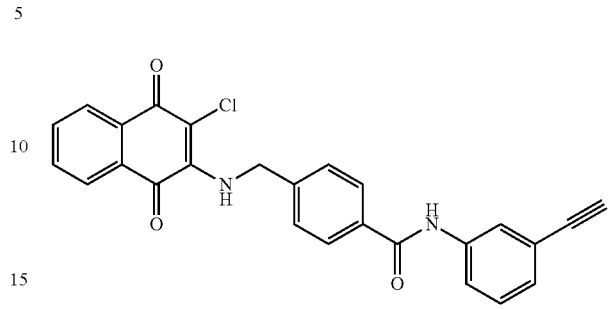

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-ethynylaniline (0.15 g, 1.32 mmol) at room temperature and the mixture was stirred overnight. The residue was purified by flash column over silica gel (ethyl acetate:n-hexane=1:4, Rf=0.25) to afford 16 (0.12 g, 30.93%) as a red solid. $^1$H-NMR (300 MHz, DMSO-$d_6$): δ 4.17 (s, 1H), 5.03 (s, 2H), 7.18 (d, J=7.5 Hz, 1H), 7.34 (t, J=8.1 Hz, 1H), 7.45 (d, J=8.4 Hz, 2H), 7.87 (m, 8H), 8.11 (br, 1H), 10.27 (s, 1H).

Example 14 4-(((3-chloro-1,4-dioxo-1,4-dihydronaphthalen-2-yl)amino)methyl)-N-(2-fluoro-4-iodophenyl)benzamide (17)

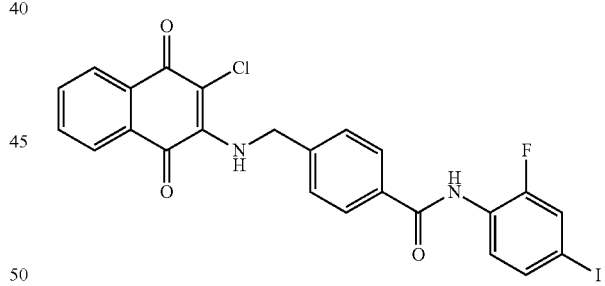

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-fluoro-4-iodoaniline (0.31 g, 1.32 mmol) at room temperature and the mixture was stirred overnight. The residue was purified by flash column over silica gel (ethyl acetate:n-hexane=1:2, Rf=0.45) to afford 17 (0.02 g, 4.05%) as a red solid. $^1$H-NMR (300 MHz, CDCl$_3$): δ 5.03 (d, J=6.9 Hz, 2H), 7.41 (m, 3H), 7.56 (m, 1H), 7.73 (m, 1H), 7.81 (m, 1H), 7.90 (d, J=8.4 Hz, 2H), 7.96 (m, 2H), 8.10 (m, 1H), 10.09 (s, 1H).

Example 15 N-(1H-benzo[d]imidazol-5-yl)-4-((3-chloro-1,4-dioxo-1,4-dihydronaphthalen-2-ylamino)methyl)benzamide (18)

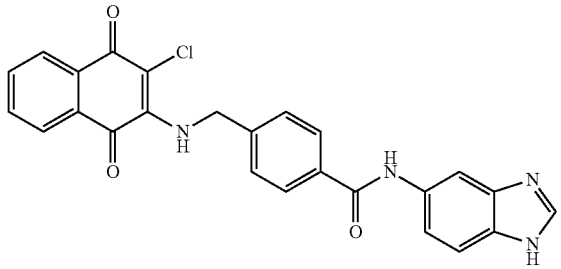 [SMILES: O=C(Nc1ccc2[nH]cnc2c1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-aminobenzimidazole (0.18 g, 1.32 mmol) at room temperature and the mixture was stirred overnight. The residue was filtered by suction filtration to yield a red product. The residue was filtered without further purification to afford 18 (0.26 g, 64.67%) as a red solid. $^1$H-NMR (300 MHz, DMSO-$d_6$): δ 5.03 (d, J=7.2 Hz, 2H), 7.43-7.48 (m, 3H), 7.54 (d, J=8.7 Hz, 1H), 7.72-7.77 (m, 1H), 7.80-7.85 (m, 1H), 7.91 (d, J=8.4 Hz, 2H), 7.96-7.99 (m, 2H), 8.09-8.15 (m, 2H), 8.20 (s, 1H), 10.20 (s, 1H).

Example 16 2-(4-(3-amino-1H-pyrazole-1-carbonyl)benzylamino)-3-chloronaphthalene-1,4-dione (19)

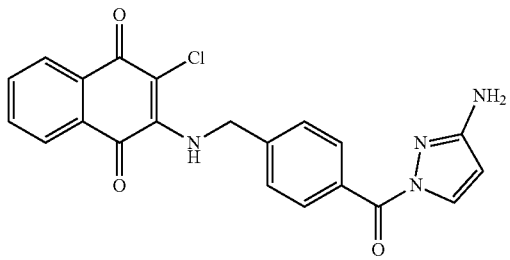 [SMILES: Nc1ccn(C(=O)c2ccc(CNC3=C(Cl)C(=O)c4ccccc4C3=O)cc2)n1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-aminopyrazole (0.11 g, 1.32 mmol) at room temperature and the mixture was stirred overnight. The residue was filtered by suction filtration to yield a red product. The residue was filtered without further purification to afford 19 (0.17 g, 47.49%) as a red solid. $^1$H-NMR (300 MHz, DMSO-$d_6$): δ 5.03 (s, 2H), 5.64 (s, 2H), 5.99 (d, J=3.0 Hz, 1H), 7.42 (d, J=8.4 Hz, 2H), 7.71-7.77 (m, 1H), 7.79-7.85 (m, 1H), 7.92-7.98 (m, 4H), 8.11 (s, 1H), 8.15 (d, J=3.0 Hz, 1H).

Example 17 4-((3-chloro-1,4-dioxo-1,4-dihydronaphthalen-2-ylamino)methyl)-N-cyclopropyl-benzamide (20)

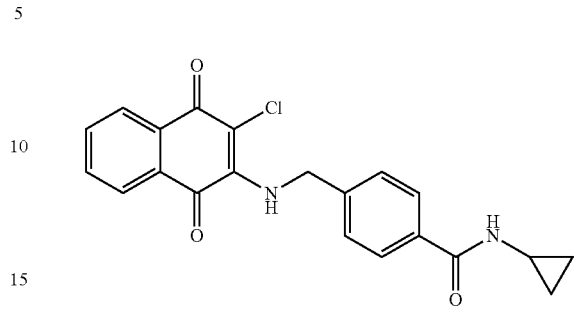

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added cyclopropylamine (0.09 ml, 1.32 mmol) at room temperature and the mixture was stirred overnight. The residue was filtered by suction filtration to yield a red product. The residue was filtered without further purification to afford 20 (0.12 g, 35.81%) as a red solid. $^1$H-NMR (300 MHz, DMSO-$d_6$): δ 0.52-0.55 (m, 2H), 0.63-0.69 (m, 2H), 2.77-2.83 (m, 1H), 4.98 (s, 2H), 7.34 (d, J=8.4 Hz, 2H), 7.72-7.75 (m, 3H), 7.82 (t, J=7.5 Hz, 1H), 7.96 (d, J=7.8 Hz, 2H), 8.05 (s, 1H), 8.36 (d, J=4.2 Hz, 1H).

Example 18 4-((3-chloro-1,4-dioxo-1,4-dihydronaphthalen-2-ylamino)methyl)-N-cyclopentyl-benzamide (21)

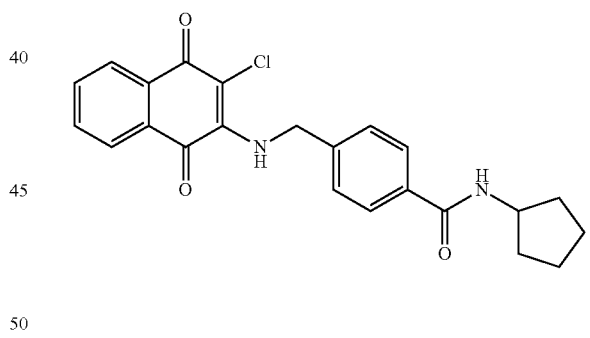

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added cyclopentylamine (0.13 ml, 1.32 mmol) at room temperature and the mixture was stirred overnight. The residue was filtered by suction filtration to yield a red product. The residue was filtered without further purification to afford 21 (0.25 g, 69.48%) as a red solid. $^1$H-NMR (300 MHz, DMSO-$d_6$): δ 1.50-1.56 (m, 4H), 1.66 (br, 2H), 1.80-1.89 (m, 2H), 4.15-4.22 (m, 1H), 4.98 (s, 2H), 7.35 (d, J=8.4 Hz, 2H), 7.71-7.84 (m, 4H), 7.96 (d, J=7.8 Hz, 2H), 8.06 (s, 1H), 8.19 (d, J=7.2 Hz, 1H).

Example 19 4-((3-chloro-1,4-dioxo-1,4-dihydronaphthalen-2-ylamino)methyl)-N-(1H-indazol-5-yl)benzamide (22)

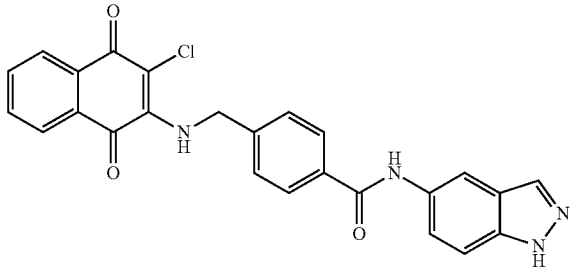

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-aminobenzindazole (0.18 g, 1.32 mmol) at room temperature and the mixture was stirred overnight. The residue was filtered by suction filtration to yield a red product. The residue was filtered without further purification to afford 22 (0.20 g, 49.74%) as a red solid. $^1$H-NMR (300 MHz, DMSO-$d_6$): δ 5.04 (d, J=7.2 Hz, 2H), 7.43-7.51 (m, 3H), 7.59-7.62 (m, 1H), 7.72-7.77 (m, 1H), 7.80-7.85 (m, 1H), 7.90-7.99 (m, 4H), 8.03 (s, 1H), 8.13 (t, J=7.2 Hz, 1H), 8.21 (s, 1H), 10.20 (s, 1H), 12.99 (s, 1H).

Example 20 4-((3-chloro-1,4-dioxo-1,4-dihydronaphthalen-2-ylamino)methyl)-N-(5-methylthiazol-2-yl)benzamide (23)

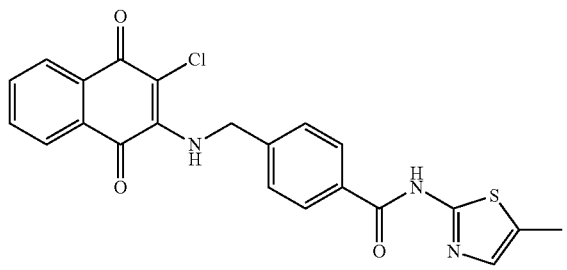 [SMILES: Cc1cnc(NC(=O)c2ccc(CNC3=C(Cl)C(=O)c4ccccc4C3=O)cc2)s1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-amino-5-methylthiazole (0.15 g, 1.32 mmol) at room temperature and the mixture was stirred overnight. The residue was filtered by suction filtration to yield a red product. The residue was filtered without further purification to afford 23 (0.38 g, 98.61%) as a red solid. $^1$H-NMR (300 MHz, DMSO-$d_6$): δ 2.36 (s, 3H), 5.03 (d, J=7.2 Hz, 2H), 7.20 (s, 1H), 7.45 (d, J=8.1 Hz, 2H), 7.72-7.78 (m, 1H), 7.80-7.85 (m, 1H), 7.50-7.99 (m, 2H), 8.03 (d, J=8.1 Hz, 2H), 8.10 (t, J=8.1 Hz, 1H), 12.21 (br, 1H).

Example 21 4-((3-chloro-1,4-dioxo-1,4-dihydronaphthalen-2-ylamino)methyl)-N-(5-methyl-3H-pyrazol-3-yl)benzamide (24)

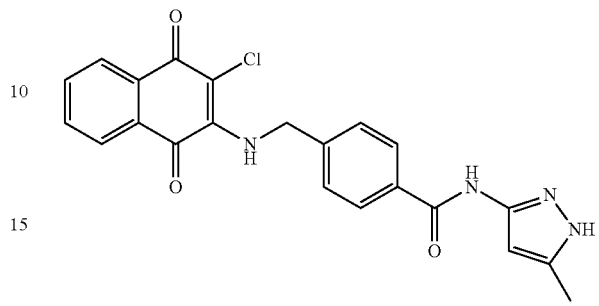

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-amino-5-methylpyrazole (0.13 g, 1.32 mmol) at room temperature and the mixture was stirred overnight. The residue was purified by flash column over silica gel (ethyl acetate:n-hexane=1:9, Rf=0.20) to afford 24 (0.05 g, 13.50%) as a red solid. $^1$H-NMR (300 MHz, CDCl$_3$): δ 5.14 (d, J=6.3 Hz, 2H), 5.34 (s, 1H), 5.60 (br, 2H), 6.29 (br, 1H), 7.44 (d, J=8.4 Hz, 2H), 7.64-7.68 (m, 1H), 7.73-7.78 (m, 1H), 8.07 (d, J=7.8 Hz, 1H), 8.12 (d, J=8.4 Hz, 2H), 8.17 (d, J=6.3 Hz, 1H).

Example 22 2-(4-(3-amino-5-methyl-1H-pyrazole-1-carbonyl)benzylamino)-3-chloronaphthalene-1,4-dione (25)

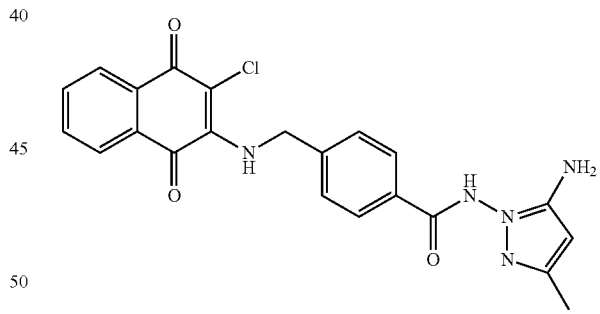

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-amino-5-methylpyrazole (0.13 g, 1.32 mmol) at room temperature and the mixture was stirred overnight. The residue was purified by flash column over silica gel (ethyl acetate:n-hexane=1:4, Rf=0.25) to afford 25 (0.04 g, 10.80%) as a red solid. $^1$H-NMR (300 MHz, DMSO-$d_6$): δ 2.49 (s, 3H), 5.03 (s, 2H), 5.44 (s, 2H), 5.78 (s, 1H), 7.38 (d, J=8.4 Hz, 2H), 7.73-7.86 (m, 4H), 7.98 (d, J=7.8 Hz, 2H), 8.10 (s, 1H).

Example 23 4-((3-chloro-1,4-dioxo-1,4-dihydronaphthalen-2-ylamino)methyl)-N-(3-nitropyridin-4-yl)benzamide (26)

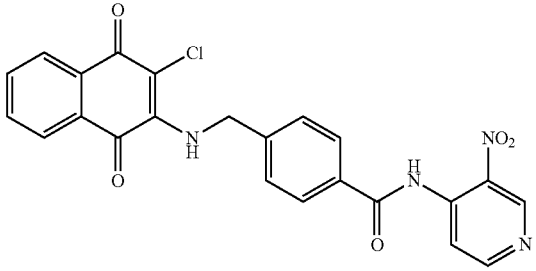 [SMILES: O=C(Nc1ccncc1[N+](=O)[O-])c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-amino-3-nitropyridine (0.18 g, 1.32 mmol) at room temperature and the mixture was stirred overnight. The residue was purified by flash column over silica gel (ethyl acetate:n-hexane=1:2, Rf=0.25) to afford 26 (0.06 g, 14.73%) as a red solid. $^1$H-NMR (300 MHz, DMSO-d$_6$): δ 5.05 (d, J=6.9 Hz, 2H), 7.52 (d, J=8.4 Hz, 2H), 7.72-7.78 (m, 1H), 7.80-7.86 (m, 1H), 7.92 (d, J=8.4 Hz, 2H), 7.96-8.00 (m, 4H), 8.13 (t, J=6.9 Hz, 1H), 8.76 (d, J=5.7 Hz, 1H), 9.12 (s, 1H), 11.07 (s, 1H).

Example 24 4-((3-chloro-1,4-dioxo-1,4-dihydronaphthalen-2-ylamino)methyl)-N-(quinolin-6-yl)benzamide (28)

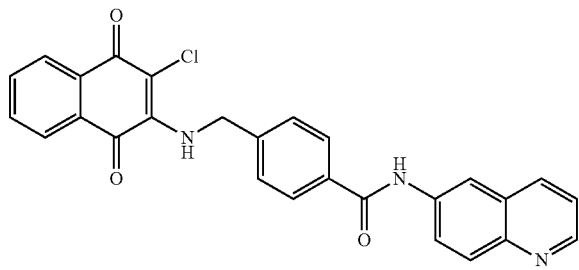 [SMILES: O=C(Nc1ccc2ncccc2c1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 6-aminoquinoline (0.19 g, 1.32 mmol) at room temperature and the mixture was stirred overnight. The residue was purified by flash column over silica gel (ethyl acetate:n-hexane=1:2, Rf=0.20) to afford 28 (0.11 g, 26.72%) as a red solid. $^1$H-NMR (300 MHz, DMSO-d$_6$): δ 5.04 (s, 2H), 7.46-7.49 (m, 3H), 7.72-7.77 (m, 1H), 7.80-7.85 (m, 1H), 7.94-8.00 (m, 6H), 8.12 (br, 1H), 8.30 (d, J=8.7 Hz, 1H), 8.51 (s, 1H), 8.78-8.80 (m, 1H), 10.52 (s, 1H).

Example 25 4-((3-chloro-1,4-dioxo-1,4-dihydronaphthalen-2-ylamino)methyl)-N-(quinolin-8-yl)benzamide (29)

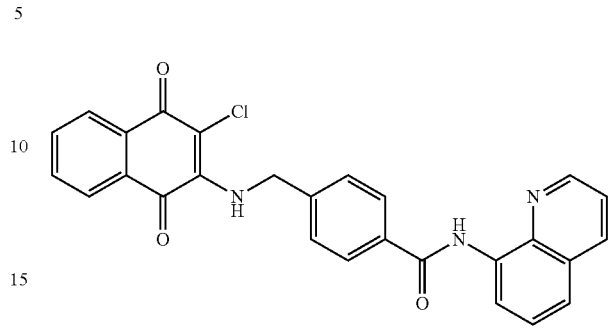

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 8-aminoquinoline (0.19 g, 1.32 mmol) at room temperature and the mixture was stirred overnight. The residue was filtered by suction filtration to yield a red product. The residue was filtered without further purification to afford 29 (0.15 g, 36.43%) as a red solid. $^1$H-NMR (300 MHz, DMSO-d$_6$): δ 5.07 (d, J=6.9 Hz, 2H), 7.55 (d, J=8.4 Hz, 2H), 7.62-7.69 (m, 2H), 7.72-7.78 (m, 2H), 7.81-7.84 (m, 1H), 7.86-8.02 (m, 4H), 8.14 (t, J=6.6 Hz, 1H), 8.44-8.47 (m, 1H), 8.70-8.73 (m, 1H), 8.94-8.95 (m, 1H), 10.62 (s, 1H).

Example 26 4-((3-chloro-1,4-dioxo-1,4-dihydronaphthalen-2-ylamino)methyl)-N-(quinolin-3-yl)benzamide (30)

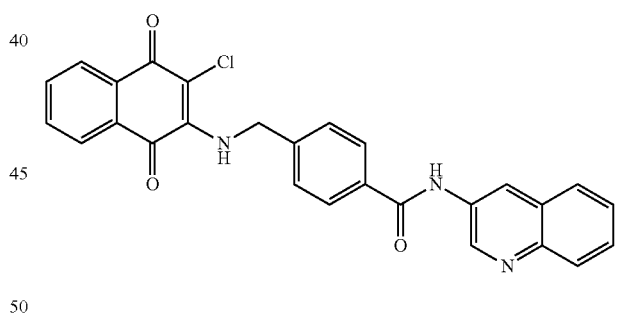

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-aminoquinoline (0.19 g, 1.32 mmol) at room temperature and the mixture was stirred overnight. The residue was purified by flash column over silica gel (ethyl acetate:n-hexane=1:2, Rf=0.43) to afford 30 (0.10 g, 24.29%) as a red solid. $^1$H-NMR (300 MHz, DMSO-d$_6$): δ 5.05 (s, 2H), 7.49 (d, J=8.4 Hz, 2H), 7.55-7.60 (m, 1H), 7.63-7.68 (m, 1H), 7.72-7.85 (m, 2H), 7.93-7.99 (m, 6H), 8.11 (br, 1H), 8.82 (s, 1H), 9.12 (s, 1H), 10.66 (br, 1H).

Example 27 4-((3-chloro-1,4-dioxo-1,4-dihydronaphthalen-2-ylamino)methyl)-N-(quinolin-5-yl)benzamide (31)

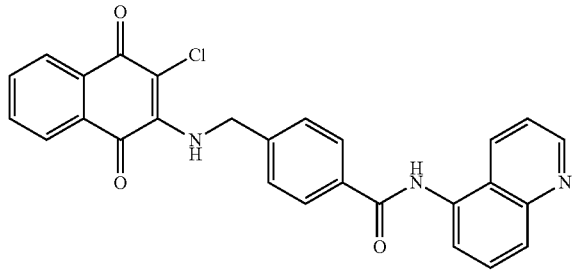 [SMILES: O=C(Nc1cccc2ncccc12)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-aminoquinoline (0.13 g, 1.32 mmol) at room temperature and the mixture was stirred overnight. The residue was purified by flash column over silica gel (ethyl acetate:n-hexane=1:2, Rf=0.20) to afford 31 (0.10 g, 24.29%) as a red solid. $^1$H-NMR (300 MHz, DMSO-$d_6$): δ 5.06 (s, 2H), 7.47-7.53 (m, 3H), 7.68 (d, J=6.9 Hz, 1H), 7.73-7.83 (m, 3H), 7.92-8.05 (m, 5H), 8.14 (s, 1H), 8.37 (d, J=8.7 Hz, 1H), 8.91 (s, 1H), 10.48 (s, 1H).

Example 28 4-((3-chloro-1,4-dioxo-1,4-dihydronaphthalen-2-ylamino)methyl)-N-(2-methylquinolin-4-yl)benzamide (32)

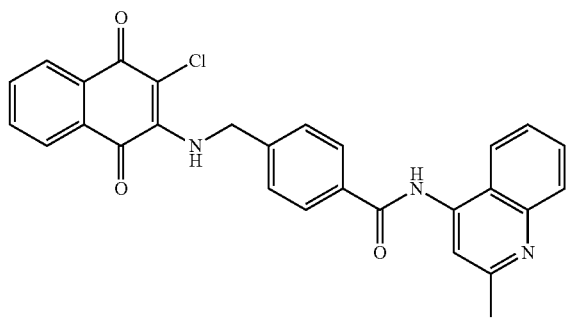 [SMILES: Cc1cc(NC(=O)c2ccc(CNC3=C(Cl)C(=O)c4ccccc4C3=O)cc2)c2ccccc2n1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-aminothiazole (0.13 g, 1.32 mmol) at room temperature and the mixture was stirred overnight. The residue was purified by flash column over silica gel (ethyl acetate:n-hexane=1:1, Rf=0.13) to afford 32 (0.22 g, 51.87%) as a red solid. $^1$H-NMR (300 MHz, DMSO-$d_6$): δ 2.65 (s, 3H), 5.07 (d, J=6.9 Hz, 2H), 7.49-7.52 (m, 3H), 7.70-7.76 (m, 2H), 7.78-7.86 (m, 2H), 7.91-7.80 (m, 3H), 8.03 (d, J=8.4 Hz, 2H), 8.13-8.18 (m, 2H), 10.54 (s, 1H).

Example 29 4-((3-chloro-1,4-dioxo-1,4-dihydronaphthalen-2-ylamino)methyl)-N-(1H-indol-5-yl)benzamide (33)

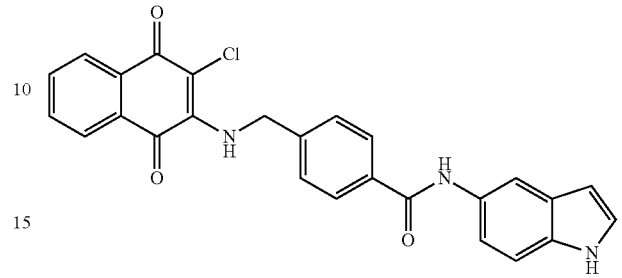

A mixture of 97 (0.26 g, 0.76 mmol), HBTU (0.43 g, 1.13 mmol), DIPEA (0.20 ml, 1.13 mmol) and DMF (2.5 ml) was stirred for a while, to which was then added 5-aminoindole (0.15 g, 1.13 mmol) at room temperature and the mixture was stirred overnight. The residue was purified by flash column over silica gel (ethyl acetate:n-hexane=2:3, Rf=0.35) to afford 33 (0.03 g, 8.66%) as a red solid. $^1$H-NMR (300 MHz, DMSO-$d_6$): δ 5.04 (d, J=6.6 Hz, 2H), 6.39 (s, 1H), 7.30-7.38 (m, 3H), 7.44 (d, J=8.1 Hz, 2H), 7.73-7.78 (m, 1H), 7.81-7.86 (m, 1H), 7.91 (d, J=8.4 Hz, 2H), 7.96-8.00 (m, 3H), 8.11 (s, 1H), 10.02 (s, 1H), 11.01 (s, 1H).

Example 30 4-((3-chloro-1,4-dioxo-1,4-dihydronaphthalen-2-ylamino)methyl)-N-(2-methyl-1H-indol-5-yl)benzamide (34)

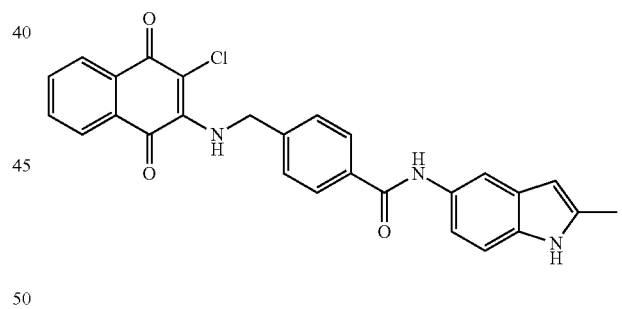

A mixture of 97 (0.26 g, 0.76 mmol), HBTU (0.43 g, 1.13 mmol), DIPEA (0.20 ml, 1.13 mmol) and DMF (2.5 ml) was stirred for a while, to which was then added 5-amino2-methylindole (0.17 g, 1.13 mmol) at room temperature and the mixture was stirred overnight. The residue was purified by flash column over silica gel (ethyl acetate: n-hexane=1:1, Rf=0.13) to afford 34 (0.08 g, 22.40%) as a red solid. $^1$H-NMR (300 MHz, DMSO-$d_6$): δ 2.36 (s, 3H), 5.03 (s, 2H), 6.08 (s, 1H), 7.18-7.28 (m, 2H), 7.43 (d, J=8.4 Hz, 2H), 7.73-7.86 (m, 3H), 7.90 (d, J=8.1 Hz, 2H), 7.95-8.00 (m, 2H), 8.11 (br, 1H), 9.96 (s, 1H), 10.82 (s, 1H).

Example 31 4-((3-chloro-1,4-dioxo-1,4-dihydronaphthalen-2-ylamino)methyl)-N-(1H-indol-7-yl)benzamide (35)

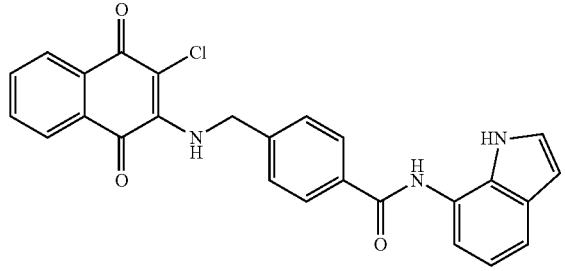

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 7-aminoindole (0.17 g, 1.32 mmol) at room temperature and the mixture was stirred overnight. The residue was purified by flash column over silica gel (ethyl acetate:n-hexane=1:1, Rf=0.13) to afford 35 (0.02 g, 4.99%) as a red solid. $^1$H-NMR (300 MHz, DMSO-$d_6$): δ 5.04 (s, 2H), 6.44 (s, 1H), 6.97 (t, J=7.8 Hz, 1H), 7.30-7.33 (m, 2H), 7.39 (d, J=7.8 Hz, 1H), 7.46 (d, J=8.1 Hz, 2H), 7.72-7.78 (m, 1H), 7.80-7.86 (m, 1H), 7.86-7.99 (m, 4H), 8.12 (br, 1H), 10.05 (s, 1H), 10.86 (s, 1H).

Example 32 4-((3-chloro-1,4-dioxo-1,4-dihydronaphthalen-2-ylamino)methyl)-N-(1H-indol-4-yl)benzamide (36)

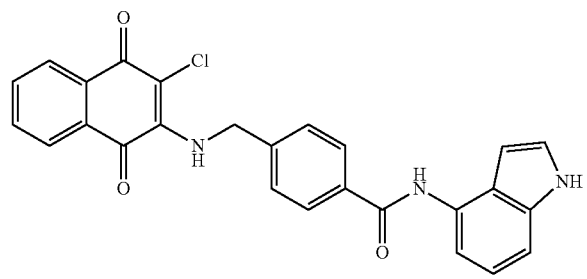 [SMILES: O=C(Nc1cccc2[nH]ccc12)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-aminoindole (0.17 g, 1.32 mmol) at room temperature and the mixture was stirred overnight. The residue was purified by flash column over silica gel (ethyl acetate:n-hexane=1:1, Rf=0.45) to afford 36 (0.30 g, 74.78%) as a red solid. $^1$H-NMR (300 MHz, DMSO-$d_6$): δ 5.04 (s, 2H), 6.56 (s, 1H), 7.04 (t, J=7.8 Hz, 1H), 7.20 (d, J=1.5 Hz, 1H), 7.27 (t, J=3.0 Hz, 1H), 7.35 (d, J=7.2 Hz, 1H), 7.44 (d, J=8.4 Hz, 2H), 7.72-7.77 (m, 1H), 7.80-7.85 (m, 1H), 7.93-7.99 (m, 4H), 8.11 (br, 1H), 9.99 (s, 1H), 11.10 (s, 1H).

Example 33 4-((3-chloro-1,4-dioxo-1,4-dihydronaphthalen-2-ylamino)methyl)-N-(4-(4-ethylpiperazin-1-yl)phenyl)benzamide (37)

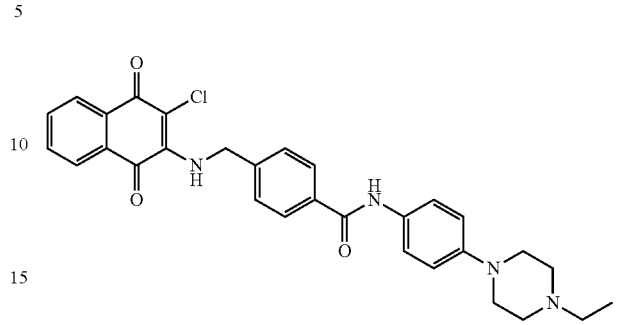

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-(4-ethylpiperazin-1-yl)aniline (0.27 g, 1.32 mmol) at room temperature and the mixture was stirred overnight. The residue was filtered by suction filtration to yield a red product. The residue was filtered without further purification to afford 37 (0.40 g, 85.92%) as a red solid. $^1$H-NMR (300 MHz, DMSO-$d_6$): δ 1.01 (t, J=7.2 Hz, 3H), 2.34 (q, J=7.2 Hz, 2H), 3.07 (br, 4H), 5.01 (s, 2H), 6.89 (d, J=9.0 Hz, 2H), 7.41 (d, J=8.1 Hz, 2H), 7.56 (d, J=9.0 Hz, 2H), 7.74 (t, J=8.1 Hz, 1H), 7.77-7.88 (m, 3H), 7.95-7.98 (m, 2H), 8.09 (s, 1H), 9.98 (s, 1H).

Example 34 4-((3-chloro-1,4-dioxo-1,4-dihydronaphthalen-2-ylamino)methyl)-N-(1H-indazol-6-yl)benzamide (38)

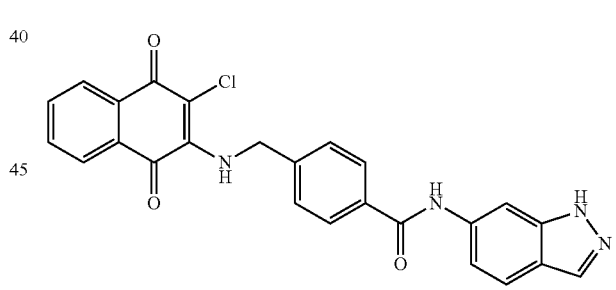

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 6-aminoindazole (0.18 g, 1.32 mmol) at room temperature and the mixture was stirred overnight. The residue was filtered by suction filtration to yield a red product. The residue was filtered without further purification to afford 38 (0.13 g, 37.94%) as a red solid. $^1$H-NMR (300 MHz, DMSO-$d_6$): δ 5.05 (s, 2H), 7.36 (d, J=8.4 Hz, 1H), 7.46 (d, J=8.1 Hz, 2H), 7.68 (d, J=8.7 Hz, 1H), 7.75 (t, J=6.9 Hz, 1H), 7.83 (t, J=6.9 Hz, 1H), 7.92 (d, J=8.1 Hz, 2H), 7.97-7.98 (m, 3H), 8.12 (br, 1H), 8.24 (s, 1H), 10.32 (s, 1H), 12.94 (s, 1H).

Example 35 4-((3-chloro-1,4-dioxo-1,4-dihydronaphthalen-2-ylamino)methyl)-N-(1H-pyrrolo[2,3-b]pyridin-5-yl)benzamide (39)

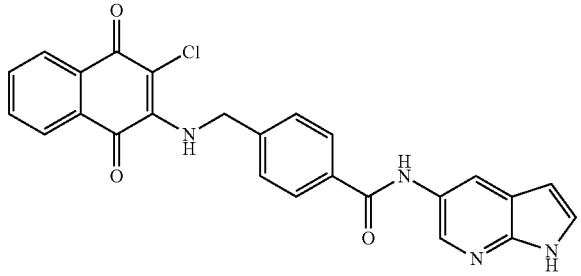 [SMILES: O=C(Nc1cnc2[nH]ccc2c1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-amino7-azaindole (0.18 g, 1.32 mmol) at room temperature and the mixture was stirred overnight. The residue was filtered by suction filtration to yield a red product. The residue was filtered without further purification to afford 39 (0.31 g, 77.10%) as a red solid. $^1$H-NMR (300 MHz, DMSO-$d_6$): δ 5.05 (d, J=7.2 Hz, 2H), 6.44 (s, 1H), 7.45-7.47 (m, 3H), 7.76 (t, J=8.1 Hz, 1H), 7.84 (t, J=7.8 Hz, 1H), 7.93-8.00 (m, 4H), 8.12 (br, 1H), 8.31 (s, 1H), 8.44 (s, 1H), 10.23 (s, 1H), 11.57 (s, 1H).

Example 36 4-((3-chloro-1,4-dioxo-1,4-dihydronaphthalen-2-ylamino)methyl)-N-(1H-pyrazolo[3,4-b]pyridin-5-yl)benzamide (40)

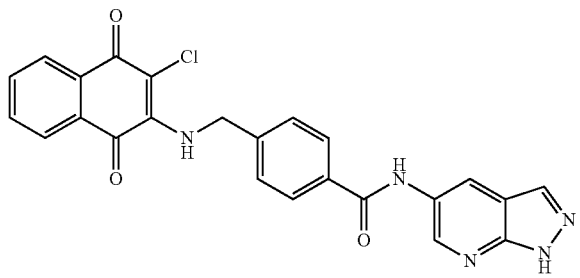 [SMILES: O=C(Nc1cnc2[nH]ncc2c1)c1ccc(CNC2=C(Cl)C(=O)c3ccccc3C2=O)cc1]

A mixture of 97 (0.28 g, 0.82 mmol), HBTU (0.47 g, 1.23 mmol), DIPEA (0.21 ml, 1.23 mmol) and DMF (2.5 ml) was stirred for a while, to which was then added 5-amino7-azaindazole (0.12 g, 0.90 mmol) at room temperature and the mixture was stirred overnight. The residue was purified by flash column over silica gel (ethyl acetate:n-hexane=2:1, Rf=0.18) to afford 40 (0.09 g, 23.97%) as a red solid. $^1$H-NMR (300 MHz, DMSO-$d_6$): δ 5.05 (s, 2H), 7.48 (d, J=8.4 Hz, 2H), 7.73-7.78 (m, 1H), 7.81-7.86 (m, 1H), 7.94-8.00 (m, 4H), 8.14 (s, 2H), 8.60 (d, J=2.4 Hz, 1H), 8.73 (d, J=2.1 Hz, 1H), 10.44 (s, 1H), 13.59 (br, 1H).

Example 37 4-((3-chloro-1,4-dioxo-1,4-dihydronaphthalen-2-ylamino)methyl)-N-(7-methyl-7H-pyrrolo[2,3-d]pyrimidin-4-yl)benzamide (41)

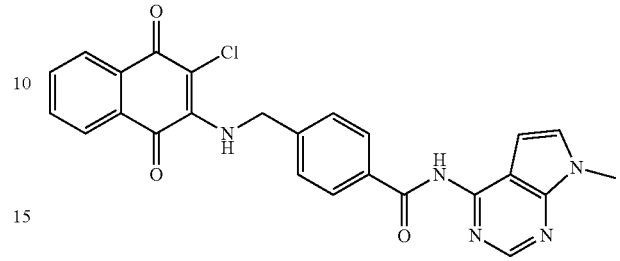

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 6-amino-1-methyl-7-deazapurine (0.20 g, 1.32 mmol) at room temperature and the mixture was stirred overnight. The residue was purified by flash column over silica gel (ethyl acetate:n-hexane=2:1, Rf=0.45) to afford 41 (0.07 g, 16.86%) as a red solid. $^1$H-NMR (300 MHz, DMSO-$d_6$): δ 3.81 (s, 3H), 5.05 (d, J=7.2 Hz, 2H), 6.61 (d, J=3.6 Hz, 1H), 7.44-7.47 (m, 3H), 7.72-7.78 (m, 1H), 7.81-7.86 (m, 1H), 7.95-8.04 (m, 4H), 8.12 (t, J=7.5 Hz, 1H), 8.57 (s, 1H), 11.00 (s, 1H).

Example 38 4-((3-chloro-1,4-dioxo-1,4-dihydronaphthalen-2-ylamino)methyl)-N-(2,3-dihydro-1H-inden-4-yl)benzamide (42)

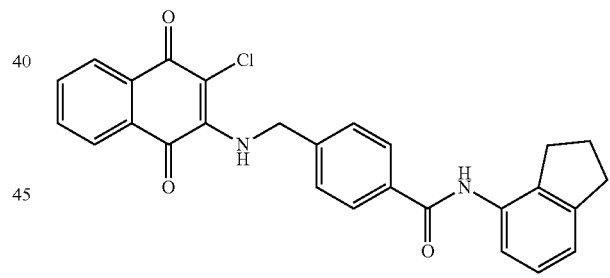

A mixture of 97 (0.30 g, 0.88 mmol), HBTU (0.50 g, 1.32 mmol), DIPEA (0.13 ml, 1.32 mmol) and DMF (2.5 ml) was stirred for a while, to which was then added 4-aminoindane (0.24 ml, 1.32 mmol) at room temperature and the mixture was stirred overnight. The residue was filtered by suction filtration to yield a red product. The residue was filtered without further purification to afford 42 (0.33 g, 82.07%) as a red solid. $^1$H-NMR (300 MHz, DMSO-$d_6$): δ 1.89-1.98 (m, 2H), 2.81 (t, J=7.5 Hz, 2H), 2.88 (t, J=7.5 Hz, 2H), 5.02 (d, J=7.2 Hz, 2H), 7.05-7.13 (m, 2H), 7.22 (d, J=7.5 Hz, 1H), 7.42 (d, J=8.1 Hz, 2H), 7.71-7.76 (m, 1H), 7.79-7.85 (m, 1H), 7.89 (d, J=8.4 Hz, 2H), 7.95-7.98 (m, 2H), 8.10 (t, J=7.5 Hz, 1H), 9.82 (s, 1H).

Example 39 4-(((3-bromo-1,4-dioxo-1,4-dihydronaphthalen-2-yl)amino)methyl)-N-(pyridin-2-yl)benzamide (6)

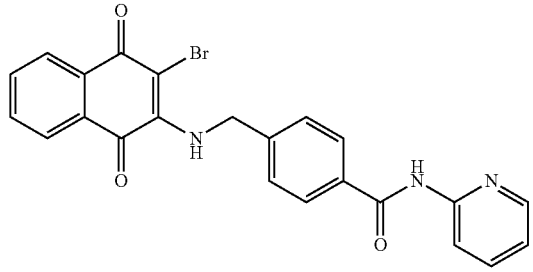 [SMILES: O=C(Nc1ccccn1)c1ccc(CNC2=C(Br)C(=O)c3ccccc3C2=O)cc1]

A mixture of 2,3-dibromo-1,4-naphthaquinone (0.31 g, 0.97 mmol), 4-(aminomethyl)-N-(pyridin-2-yl)benzamide (0.20 g, 0.88 mmol) and EtOH (10 ml) was stirred and refluxed overnight. The residue was purified by flash column over silica gel (ethyl acetate:n-hexane=1:2, Rf=0.20) to afford 6 (0.13 g, 31.95%) as a red solid. $^1$H-NMR (300 MHz, DMSO-$d_6$): δ 5.05 (d, J=7.2 Hz, 2H), 7.14 (m, 1H), 7.41 (d, J=8.1 Hz, 2H), 7.73 (t, J=7.5 Hz, 1H), 7.81 (m, 2H), 7.97 (m, 5H), 8.15 (d, J=8.1 Hz, 1H), 8.36 (d, J=4.8 Hz, 1H), 10.69 (s, 1H).

Example 40 tert-butyl 4-(pyrimidin-4-ylcarbamoyl)benzylcarbamate (100)

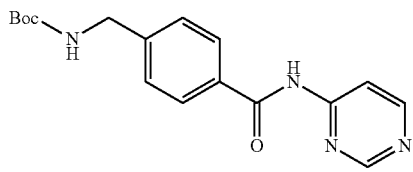 [SMILES: CC(C)(C)OC(=O)NCc1ccc(C(=O)Nc2ccncn2)cc1]

4-(aminomethyl)benzoic acid (5.0 g, 32.95 mmol) was added slowly to the corresponding sodium hydroxide (1.45 g, 36.25 mmole) and di-t-butyl-dicarbonate (7.95 g, 36.25 mmol) in H$_2$O (62.5 ml) and THF (25 ml) at 0° C. The reaction mixture was warmed to room temperature, and stirring was continued for another 18 h. The solution was evaporated to give a residue. To the residue, DMF (0.36 mL), pyridine (18 mL), oxalyl chloride (6.24 ml) and toluene (144 ml) were added and the mixture was stirred at rt for 6 hrs. The solution was filtered, washed with toluene, and the filtrate evaporated to give a residue. To the residue, pyridine (112 mL), and 4-aminopyrimidine (3.74 g, 39.4 mmol) were added and the mixture was stirred at room temperature for 16 hrs. The solution was evaporated to give a residue, which was purified by flash column over silica gel (EtOAc:n-hexane=2:3) to afford 100 (3.03 g, 28.00%). $^1$H NMR (300 MHz, CDCl$_3$): δ 1.48 (s, 3H), 4.41 (d, J=6.0 Hz, 2H), 5.02 (brs, 1H), 7.45 (d, J=8.4 Hz, 2H), 7.91 (d, J=8.1 Hz, 2H), 8.33-8.36 (m, 1H), 8.69 (d, J=5.7 Hz, 1H), 8.72 (brs, 1H), 8.88 (s, 1H).

Example 41 tert-butyl 4-(pyrazin-2-ylcarbamoyl)benzylcarbamate (101)

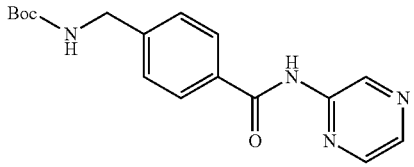 [SMILES: CC(C)(C)OC(=O)NCc1ccc(C(=O)Nc2cnccn2)cc1]

4-(aminomethyl)benzoic acid (5.0 g, 32.95 mmol) was added slowly to the corresponding sodium hydroxide (1.45 g, 36.25 mmol) and di-t-butyl-dicarbonate (7.95 g, 36.25 mmol) in H$_2$O (62.5 ml) and THF (25 mL) at 0° C. The reaction mixture was warmed to room temperature, and stirring was continued for another 18 h. The solution was evaporated to give a residue. To the residue, DMF (0.36 ml), pyridine (18 ml), oxalyl chloride (6.24 ml) and toluene (144 ml) were added and the mixture was stirred at room temperature for 6 hrs. The solution was filtered, washed with toluene, and the filtrate evaporated to give a residue. To the residue, pyridine (112 ml), and 2-aminopyrazine (3.74 g, 39.4 mmol) were added and the mixture was stirred at room temperature for 16 hrs. The residue was purified by flash column over silica gel (EtOAc:n-hexane=2:3) to afford 101 (3.90 g, 36.05%). $^1$H NMR (300 MHz, DMSO-$d_6$): δ 1.44 (s, 3H), 4.37 (d, J=5.4 Hz, 2H), 4.98 (brs, 1H), 7.41 (d, J=8.4 Hz, 2H), 7.88 (d, J=8.4 Hz, 2H), 8.23-8.25 (m, 1H), 8.34-8.36 (m, 1H), 8.54 (s, 1H), 9.67 (s, 1H).

Example 42 4-(((3-chloro-1,4-dioxo-1,4-dihydronaphthalen-2-yl)amino)methyl)-N-(pyrimidin-4-yl)benzamide (7)

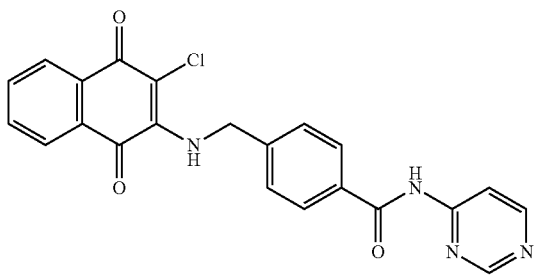

A mixture of 2,3-dichloro-1,4-naphthoquinone (0.25 g, 1.10 mmol) and 100 (0.28 g, 1.23 mmol) and ethanol (10 ml) was refluxed for 16 h. The reaction mixture was filtered washed. The residue was filtered without further purification to afford 7 (0.08 g, 17.36%) as a red solid. $^1$H NMR (300 MHz, DMSO-$d_6$): δ 5.04 (d, J=6.6 Hz, 2H), 7.45 (d, J=8.1 Hz, 2H), 7.72-7.85 (m, 2H), 7.97-7.99 (m, 4H), 8.11 (m, 1H), 8.19 (d, J=4.5 Hz, 1H), 8.70 (d, J=5.4 Hz, 1H), 8.93 (s, 1H), 11.18 (s, 1H).

Example 43 4-(((3-chloro-1,4-dioxo-1,4-dihydronaphthalen-2-yl)amino)methyl)-N-(pyrazin-2-yl)benzamide (8)

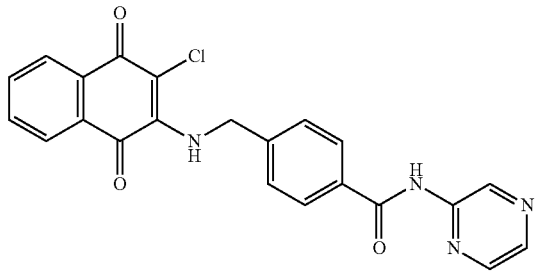 [SMILES: O=C(Nc1cnccn1)c1ccc(CNC2=C(Cl)C(=O)c3ccccc3C2=O)cc1]

A mixture of 2,3-dichloro-1,4-naphthoquinone (1.19 g, 5.26 mmol) and 101 (1.5 g, 6.57 mmol) and ethanol (20 ml) was refluxed for 16 h. The reaction mixture was filtered and washed. The residue was filtered without further purification to afford 8 (0.48 g, 21.79%) as a red solid. $^1$H NMR (300 MHz, DMSO-d$_6$): δ 5.04 (d, J=7.2 Hz, 2H), 7.45 (d, J=8.4 Hz, 2H), 7.74-7.85 (m, 2H), 7.95-8.01 (m, 4H), 8.11 (t, J=6.9 Hz, 1H), 8.40 (d, J=2.4 Hz, 1H), 8.44-8.46 (m, 1H), 9.39 (d, J=1.5 Hz, 1H), 11.04 (s, 1H).

Example 44 4-((3-chloro-1,4-dioxo-1,4-dihydronaphthalen-2-ylamino)methyl)-N-(pyridin-4-ylmethyl)benzamide (27)

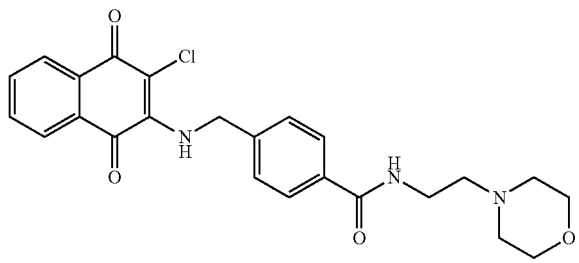 [SMILES: O=C(NCCN1CCOCC1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-aminomethylpyridine (0.13 ml, 1.32 mmol) at room temperature and stirred overnight. The residue was purified by flash column over silica gel (dichloromethane:methanol=9:1, Rf=0.48) to afford 27 (0.31 g, 81.57%) as a red solid. $^1$H-NMR (300 MHz, DMSO-d$_6$): δ 4.47 (d, J=6.0 Hz, 2H), 5.01 (s, 1H), 7.28 (d, J=5.7 Hz, 2H), 7.41 (d, J=8.1 Hz, 2H), 7.75 (t, J=6.3 Hz, 1H), 7.80-7.87 (m, 3H), 7.97 (d, J=7.8 Hz, 2H), 8.08 (s, 1H), 8.48 (d, J=6.0 Hz, 2H), 9.08 (t, J=6.0 Hz, 1H).

Example 45 4-((3-chloro-1,4-dioxo-1,4-dihydronaphthalen-2-ylamino)methyl)-N-(2-morpholinoethyl)benzamide (43)

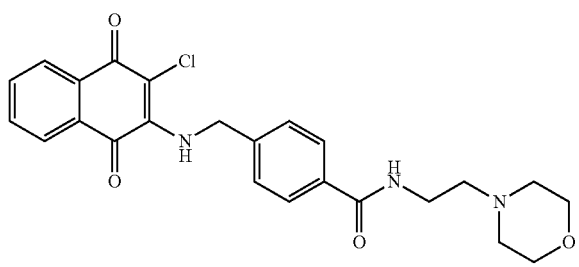 [SMILES: O=C(NCCN1CCOCC1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.13 ml, 1.32 mmol) and DMF (2.5 ml) was stirred for a while, to which was then added 2-morpholinoethanamine (0.17 ml, 1.32 mmol) at room temperature, and the mixture was stirred overnight. The residue was filtered by suction filtration to yield a red product. The residue was without further purification to afford 43 (0.23 g, 57.58%) as a red solid. $^1$H-NMR (300 MHz, DMSO-d$_6$): δ 2.38-2.45 (m, 6H), 3.54 (s, 4H), 4.99 (s, 2H), 7.36 (d, J=8.1 Hz, 2H), 7.71-7.84 (m, 4H), 7.96 (d, J=7.5 Hz, 2H), 8.05 (s, 1H), 8.33 (t, J=5.1 Hz, 1H).

Example 46 N-(2-(1H-indol-3-yl)ethyl)-4-((3-chloro-1,4-dioxo-1,4-dihydronaphthalen-2-ylamino)methyl)benzamide (44)

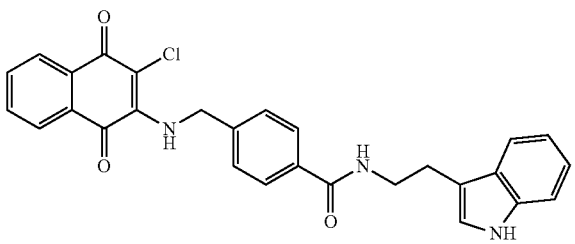 [SMILES: O=C(NCCc1c[nH]c2ccccc12)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.13 ml, 1.32 mmol) and DMF (2.5 ml) was stirred for a while, to which was then added 2-aminothiazole (0.21 g, 1.32 mmol) at room temperature and stirred overnight. The residue was purified by flash column over silica gel (ethyl acetate:n-hexane=2:1, Rf=0.45) to afford 44 (0.13 g, 30.53%) as a red solid. $^1$H-NMR (300 MHz, DMSO-d$_6$): δ 2.72-2.94 (m, 2H), 3.47-3.54 (m, 2H), 4.99 (s, 2H), 6.92-6.98 (m, 1H), 7.01-7.07 (m, 1H), 7.15 (d, J=2.4 Hz, 1H), 7.31 (d, J=8.1 Hz, 1H), 7.36 (d, J=8.1 Hz, 2H), 7.55 (d, J=7.5 Hz, 1H), 7.73-7.82 (m, 4H), 7.96 (d, J=8.1 Hz, 2H), 8.06 (s, 1H), 8.54 (t, J=5.7 Hz, 1H), 10.78 (s, 1H).

Example 47 4-(((3-chloro-1,4-dioxo-1,4-dihydronaphthalen-2-yl)amino)methyl)-N-(2-(dimethylamino)ethyl)benzamide (45)

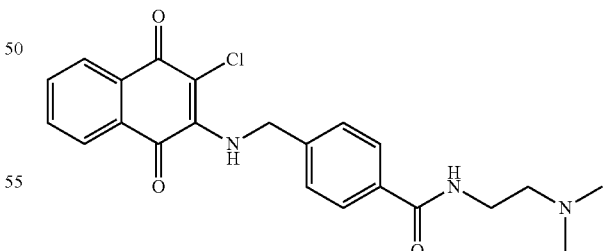

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-Dimethylaminoethylamine (0.12 ml, 1.06 mmol) at room temperature and stirred overnight. The residue was purified by flash column over silica gel (dichloromethane:methanol=9:1, Rf=0.33) to afford 45 (0.05 g, 13.79%) as a red solid. $^1$H-NMR (300 MHz, CD₃OD): δ 2.92 (s, 6H), 3.72 (t, J=6.0 Hz, 2H), 5.10 (s, 2H), 7.44 (d, J=8.4 Hz, 2H), 7.68-7.81 (m, 2H), 7.85 (d, J=8.4 Hz, 2H), 8.02-8.06 (m, 2H).

Example 48 4-(((3-chloro-1,4-dioxo-1,4-dihydronaphthalen-2-yl)amino)methyl)-N-(2-(pyrrolidin-1-yl)ethyl)benzamide (46)

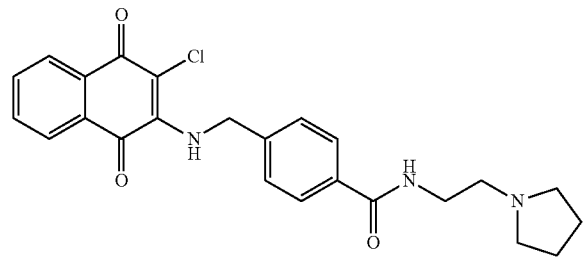 [SMILES: O=C(NCCN1CCCC1)c1ccc(CNC2=C(Cl)C(=O)c3ccccc3C2=O)cc1]

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-(pyrrolidin-1-yl)ethanamine (0.13 ml, 1.06 mmol) at room temperature and stirred overnight. The residue was purified by flash column over silica gel (dichloromethane:methanol=9:1, Rf=0.33) to afford 46 (0.22 g, 57.09%) as a red solid. ¹H-NMR (300 MHz, DMSO-d₆): δ 1.89 (s, 4H), 3.22-3.25 (m, 5H), 3.54-3.60 (m, 3H), 5.00 (t, J=7.2 Hz, 2H), 7.38 (d, J=8.1 Hz, 2H), 7.72-7.82 (m, 2H), 7.85 (d, J=8.4 Hz, 2H), 7.94-7.98 (m, 2H), 8.08 (t, J=7.2 Hz, 1H), 8.74 (t, J=5.7 Hz, 1H).

Example 49 4-(((3-chloro-1,4-dioxo-1,4-dihydronaphthalen-2-yl)amino)methyl)-N-(2-(diethylamino)ethyl)benzamide (47)

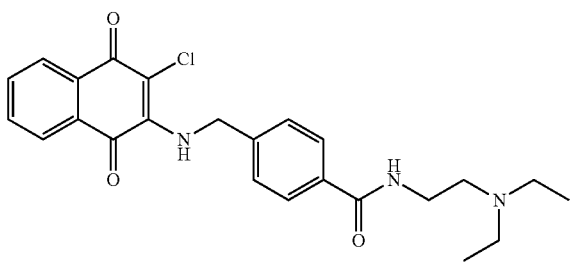 [SMILES: CCN(CC)CCNC(=O)c1ccc(CNC2=C(Cl)C(=O)c3ccccc3C2=O)cc1]

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-Diethylaminoethylamine (0.15 ml, 1.06 mmol) at room temperature and stirred overnight. The residue was purified by flash column over silica gel (dichloromethane:methanol=9:1, Rf=0.30) to afford 47 (0.06 g, 15.50%) as a red solid. ¹H-NMR (300 MHz, CD₃OD): δ 1.33 (t, J=7.2 Hz, 6H), 3.32-3.38 (m, 3H), 3.73 (t, J=6.0 Hz, 2H), 5.10 (s, 2H), 7.45 (d, J=8.1 Hz, 2H), 7.67-7.80 (m, 2H), 7.85 (d, J=8.1 Hz, 2H), 8.02-8.06 (m, 2H).

Example 50 4-(((3-chloro-1,4-dioxo-1,4-dihydronaphthalen-2-yl)amino)methyl)-N-(2-(piperidin-1-yl)ethyl)benzamide (48)

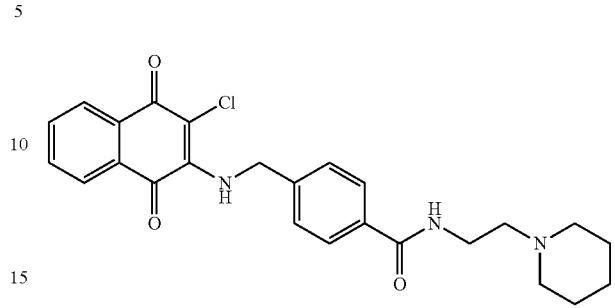

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-(piperidin-1-yl)ethanamine (0.15 ml, 1.06 mmol) at room temperature and stirred overnight. The residue was purified by flash column over silica gel (dichloromethane:methanol=9:1, Rf=0.55) to afford 48 (0.08 g, 20.11%) as a red solid. ¹H-NMR (300 MHz, DMSO-d₆): δ 1.42-1.44 (m, 2H), 1.58-1.60 (m, 4H), 2.78 (br, 6H), 3.44-3.48 (m, 2H), 4.99 (d, J=7.2 Hz, 2H), 7.37 (d, J=8.4 Hz, 2H), 7.71-7.84 (m, 4H), 7.94-7.97 (m, 2H), 8.07 (t, J=7.2 Hz, 1H), 8.53 (br, 1H).

Example 51 4-(((3-chloro-1,4-dioxo-1,4-dihydronaphthalen-2-yl)amino)methyl)-N-(2-(4-methylpiperazin-1-yl)ethyl)benzamide (49)

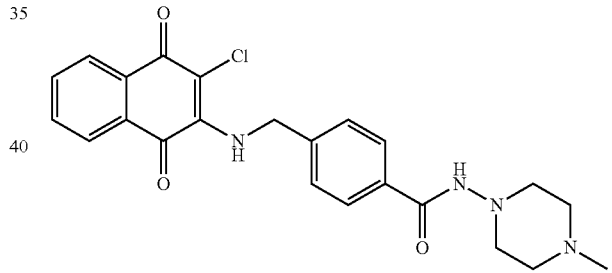

A mixture of 97 (0.30 g, 0.88 mmol), EDC.HCl (0.25 g, 1.32 mmol), HOBt (0.14 g, 1.06 mmol), NMM (0.23 ml, 2.11 mmol) and DMF (2.5 ml) was stirred for a while, to which was then added 2-(4-methylpiperazin-1-yl)ethylamine (0.16 ml, 1.06 mmol) at room temperature and stirred overnight. The residue was purified by flash column over silica gel (dichloromethane:methanol=9:1, Rf=0.19) to afford 49 (0.08 g, 19.47%) as a red solid. ¹H-NMR (300 MHz, DMSO-d₆): δ 2.13 (s, 3H), 2.36-2.42 (br, 12H), 4.91 (d, J=6.3 Hz, 2H), 7.29 (d, J=7.8 Hz, 2H), 7.67-7.77 (m, 4H), 7.88 (d, J=6.9 Hz, 2H), 7.98 (br, 1H), 8.25 (br, 1H).

Biological Assay

Cell Culture

WI-38 cells, a normal human embryonic lung fibroblast cell line, were obtained from American Type Culture Collection (Manassas, VA). Cells were grown in MEM nutrient mixture, containing 10% FCS, 2 mM L-glutamine, 0.1 mM NEAA, 1 mM sodium pyruvate, 50 U/ml penicillin G, and 100 μg/ml streptomycin, in a humidified 37° C. incubator with 5% CO₂ Cells were used between passages 18 and 30 for all experiments. After reaching confluence, cells were seeded onto 6-cm dishes for immunoblotting.

Compound Use in Assay

The compound, 4-(((3-chloro-1,4-dioxo-1,4-dihydronaphthalen-2-yl)amino)methyl)-N-(pyridin-4-yl)benzamide (MPT0L056 or L056 used herein), was used in the assay described herein.

Western Blot Analysis

Western blot analyses were performed as described previously (Chen B C, Chang Y S, Kang J C, Hsu M J, Sheu J R, Chen T L, et al. *Peptidoglycan induces nuclear factor-kappaB activation and cyclooxygenase-2 expression via Ras, Raf-1, and ERK in RAW 264.7 macrophages. J Biol Chem* 2004:279:20889-97). Briefly, WI-38 lung fibroblasts were cultured in 6-cm dishes. After reaching confluence, cells were pretreated with specific inhibitors (E028 and G009) as indicated for 30 min, and then treated with the vehicle ($H_2O$) or 10 ng/ml TGF-β for 2 h (CTGF assay) or 24 h (collagen I assay). Whole-cell lysates (30 μg) were subjected to 12% (CTGF) or 8% (collagen I) SDS-PAGE, and transferred onto a polyvinylidene difluoride membrane which was then incubated in TBST buffer (150 mM NaC, 20 mM Tris-HCl, and 0.02% Tween 20; pH 7.4) containing 5% BSA. Proteins were visualized by specific primary antibodies and then incubated with HRP-conjugated secondary antibodies. The immunoreactivity was detected using enhanced chemiluminescence (ECL) following the manufacturer's instructions. Quantitative data were obtained using a computing densitometer with scientific imaging systems (Kodak, Rochester, NY).

Statistical Analyses

Results are expressed as the mean±SEM for the indicated number of separate experiments. Means were checked for statistical difference using t-test and P-values <0.05 were considered significant.

Figure 1B:
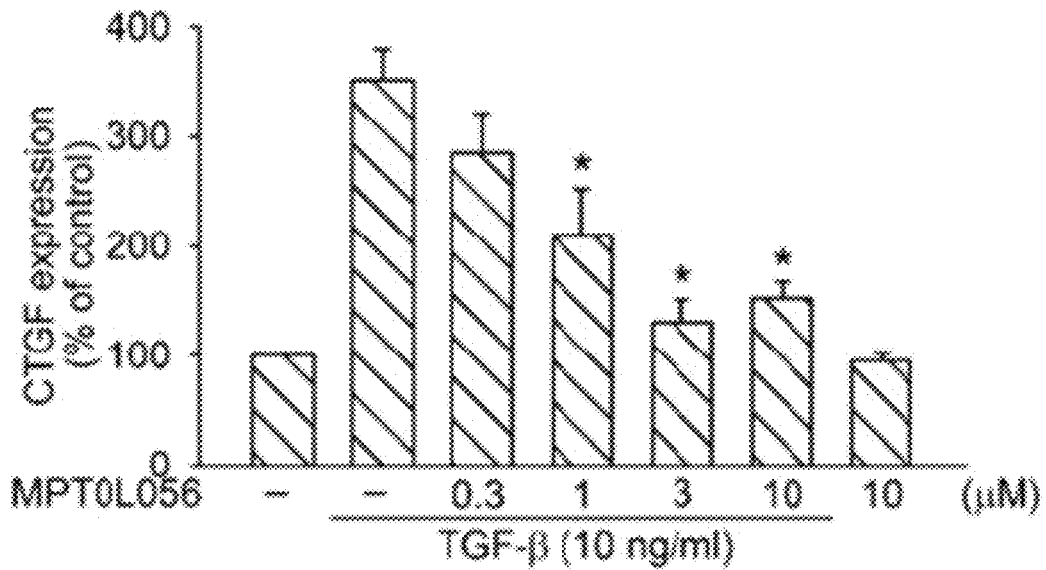
Figure 2A:
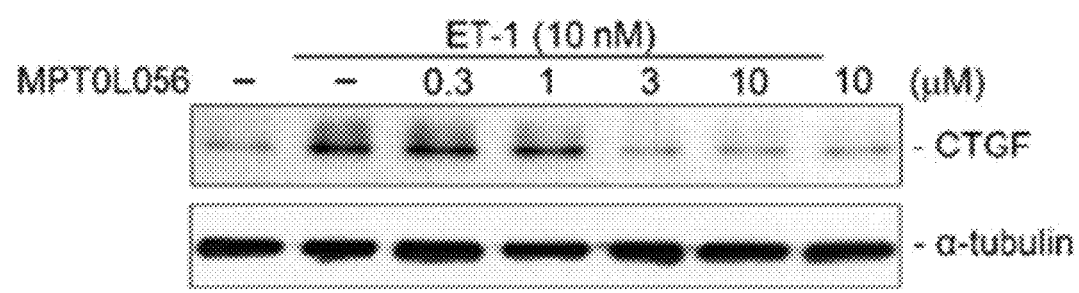
FIGS. 2(A) and 2(B) show the effects of L056 on ET-1-induced CTGF expression in WI-38 cells. WI-38 lung fibroblasts were incubated with different concentrations of L056 (0.3, 1, 3 or 10 µM) for 30 min before and during incubation for 2 h with ET-1 (10 nM). L056 significantly inhibited ET-1-induced CTGF production from WI-38 lung fibroblasts in a concentration-dependent manner.
Figure 2B:
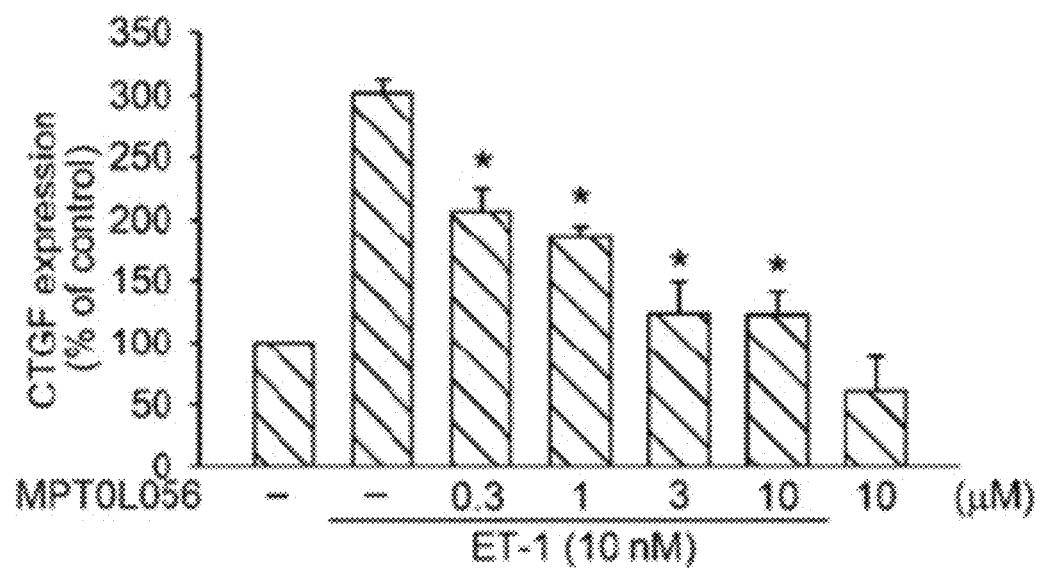
Figure 3A:
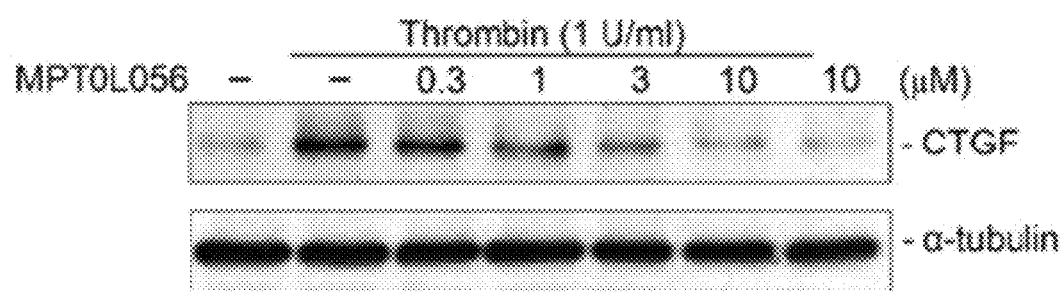
FIGS. 3(A) and 3(B) show the effects of L056 on thrombin-induced CTGF expression in WI-38 cells. WI-38 lung fibroblasts were incubated with different concentrations of L056 (0.3, 1, 3 or 10 µM) for 30 min before and during incubation for 2 h with thrombin (1 U/ml). L056 significantly inhibited thrombin-induced CTGF production from WI-38 lung fibroblasts in a concentration-dependent manner.
Figure 3B:
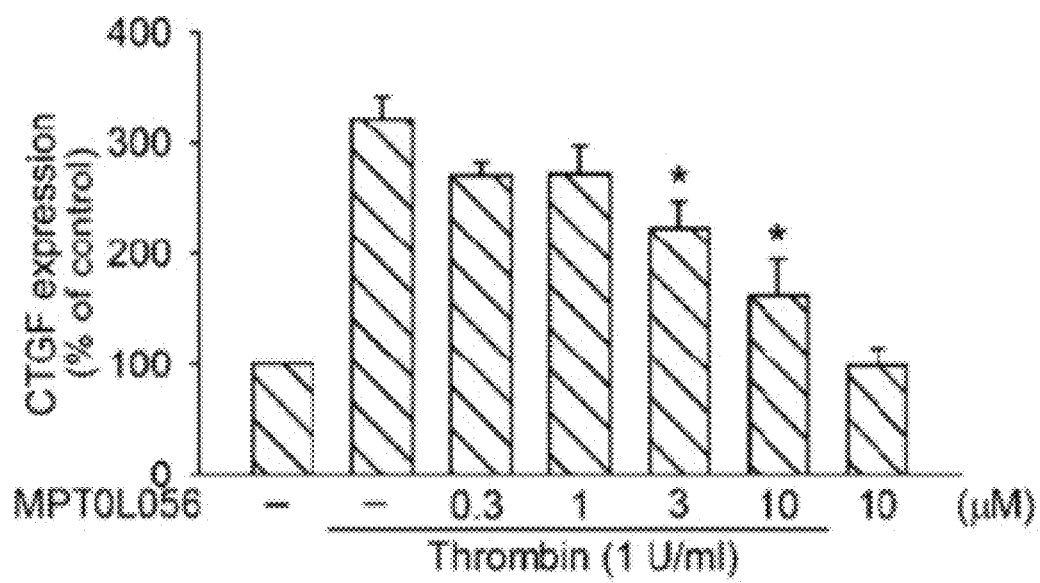
Figure 4A:
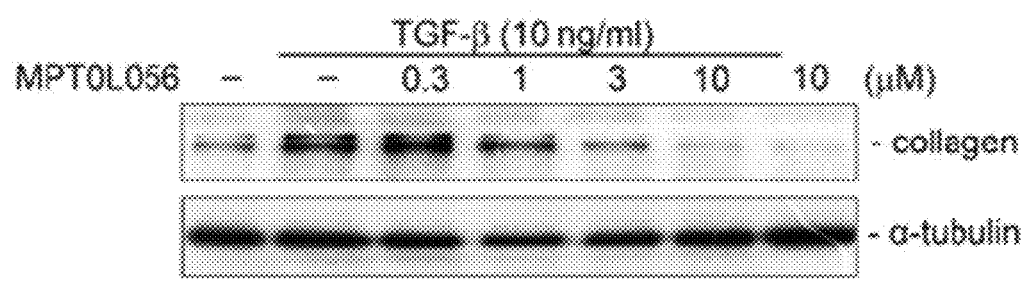
FIGS. 4(A), 4(B) and 4(C) show the effects of L056 on TGF-β-induced collagen expression in WI-38 cells. WI-38 lung fibroblasts were incubated with different concentrations of L056 (0.3, 1, 3 or 10 μM) for 30 min before and during incubation for 2 h with TGF-β (10 ng/mL). L056 significantly inhibited TGF-β-induced collagen production from WI-38 lung fibroblasts in a concentration-dependent manner.
Figure 4B:
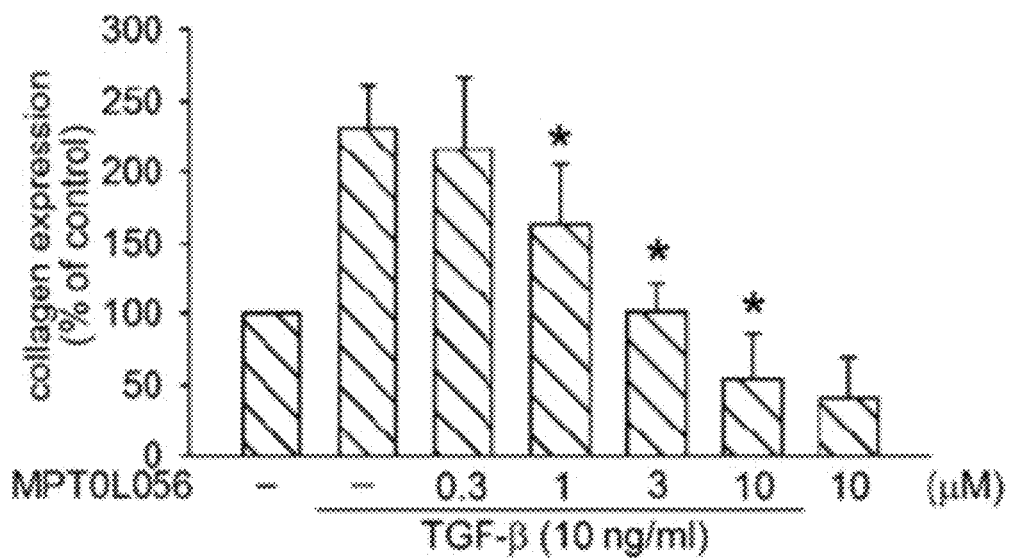
Figure 4C:
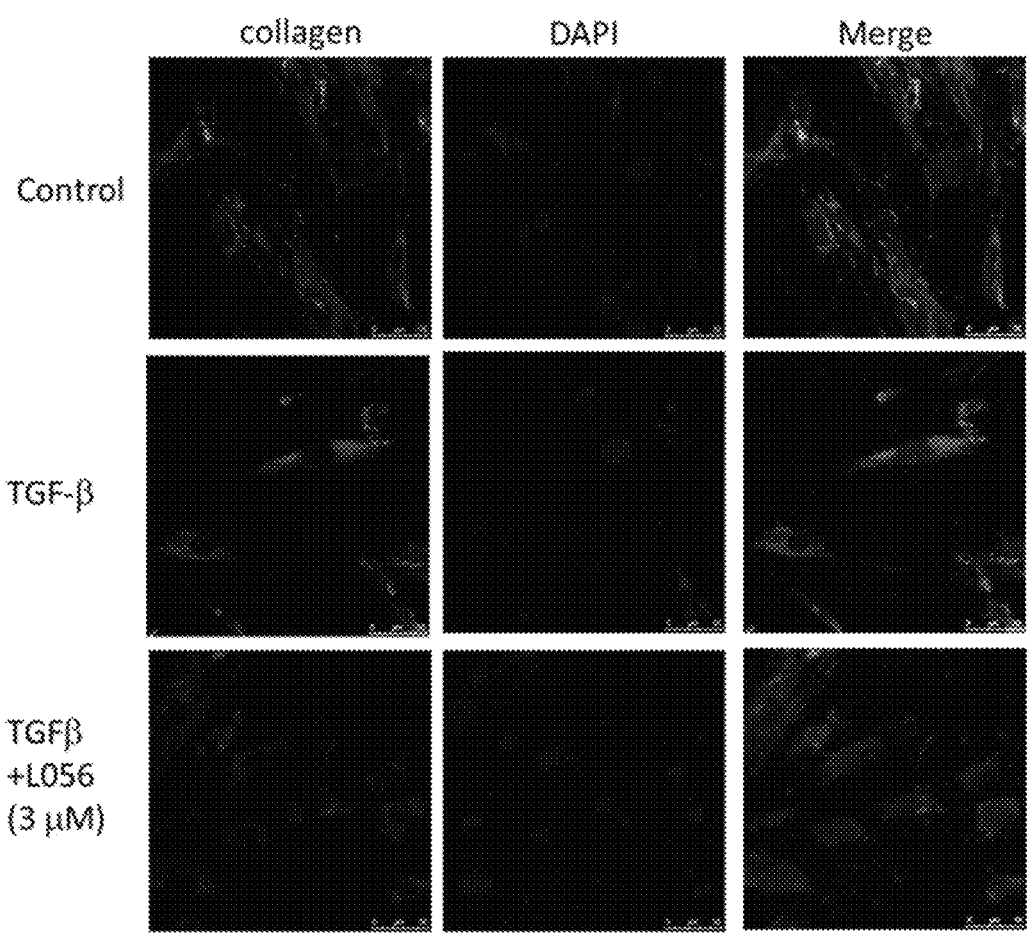

Example 1 Inhibition of Pro-fibrogenic Mediators-induced Fibrotic Protein, CTGF and Collagen I Production To determine whether the inhibitory effects of the compound MPT0L056 on pro-fibrogenic mediators (TGF-β, thrombin, and ET-1) were related to the modulation of CTGF and Collagen I production, Western blot analysis was performed. First, WI-38 lung fibroblasts were incubated with different concentrations of MPT0L056 (0.3, 1, 3 or 10 μM) for 30 min before and during incubation for 2 h with TGF-β (10 ng/mL). L056 significantly inhibited TGF-β-induced CTGF production from WI-38 lung fibroblasts in a concentration-dependent manner (FIGS. 1A and 1B). Furthermore, we examined the effects of MPT0L056 on other pro-fibrogenic mediators. MPT0L0560 also inhibited ET-1- and thrombin-induced CTGF expression form WI-38 lung fibroblasts, as shown in FIGS. 2A and 2B and FIGS. 3A and 3B, respectively. In addition, as shown in FIGS. 4A, 4B and 4C, MPT0L056 also inhibited TGF-β-induced collagen expression in WI-38 cells. These results showed that MPT0L056 apparently inhibited pro-fibrogenic mediators-induced CTGF expression and collagen production.

Figure 5A:
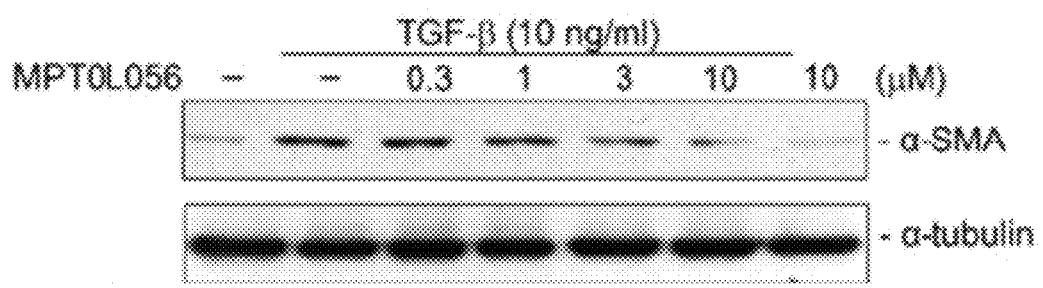
FIGS. 5(A) and 5(B) show the effects of L056 on TGF-β-induced α-SMA expression in WI-38 cells. WI-38 lung fibroblasts were incubated with different concentrations of L056 (0.3, 1, 3 or 10 μM) for 30 min before and during incubation for 2 h with TGF-β (10 ng/mL). L056 significantly inhibited TGF-β-induced α-SMA production from WI-38 lung fibroblasts in a concentration-dependent manner.
Figure 5B:
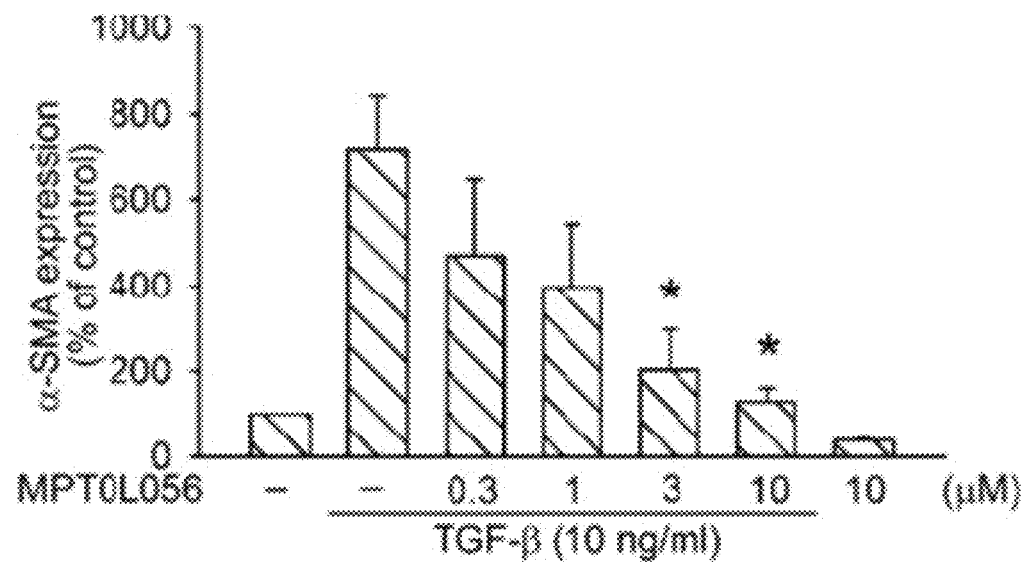
Figure 6A:
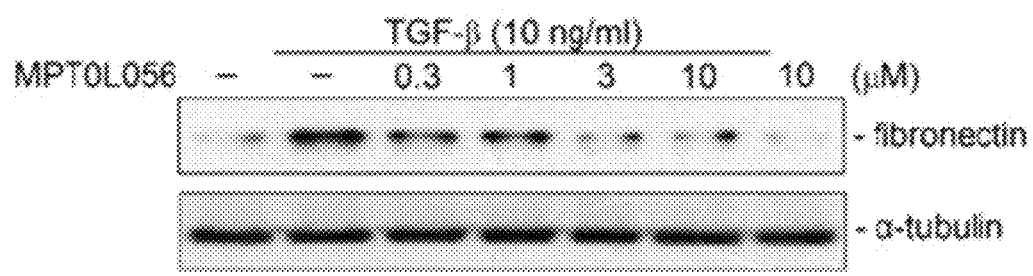
FIGS. 6(A), 6(B) and 6(C) show the effects of L056 on TGF-β-induced fibronectin expression in WI-38 cells. WI-38 lung fibroblasts were incubated with different concentrations of L056 (0.3, 1, 3 or 10 μM) for 30 min before and during incubation for 2 h with TGF-β (10 ng/mL). L056 significantly inhibited TGF-β-induced fibronectin production from WI-38 lung fibroblasts in a concentration-dependent manner.
Figure 6B:
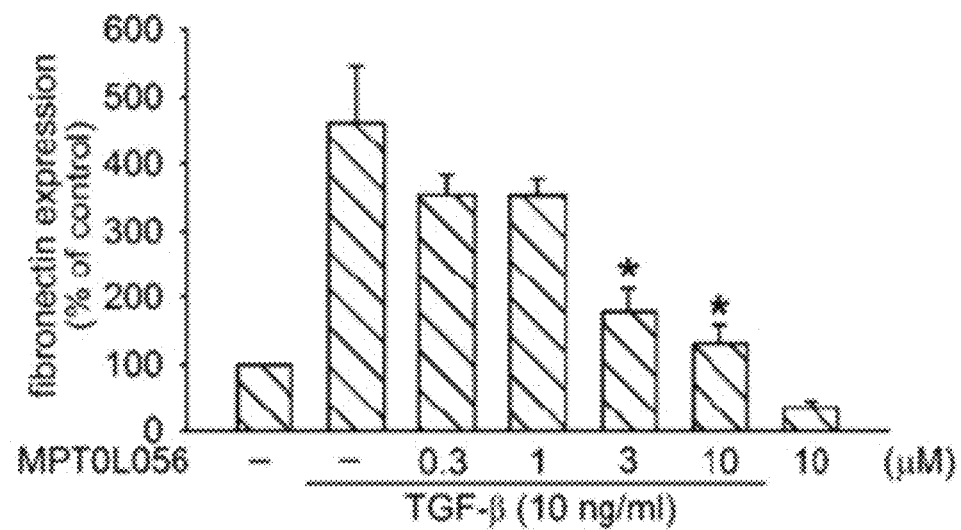
Figure 6C:
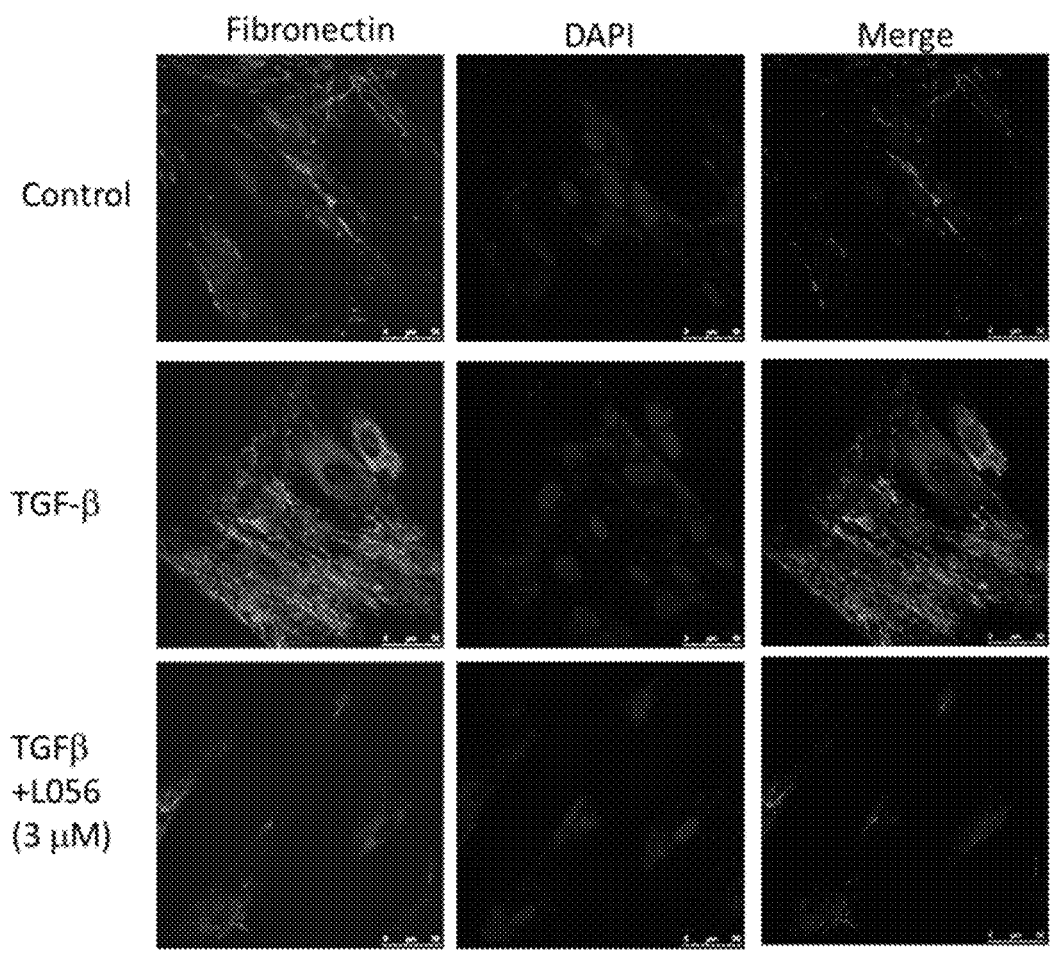

In addition, pro-fibrogenic mediators, pro-fibrogenic mediators and α-SMA, fibronectin were also examined. WI-38 lung fibroblasts were incubated with different concentrations of MPT0L056 (0.3, 1, 3 or 10 μM) for 30 min before and during incubation for 24 h with TGF-β (10 ng/mL). L056 significantly inhibited TGF-β-induced α-SMA (see FIGS. 5A and 5B) and fibronectin expression (see FIGS. 6A, 6B and 6C) from WI-38 lung fibroblasts in a concentration-dependent manner. These results suggested that MPT0L056 inhibited TGF-β-mediated fibrogenic protein expression in WI-38 cells.

Example 2 Cell Viability Test

Figure 7:
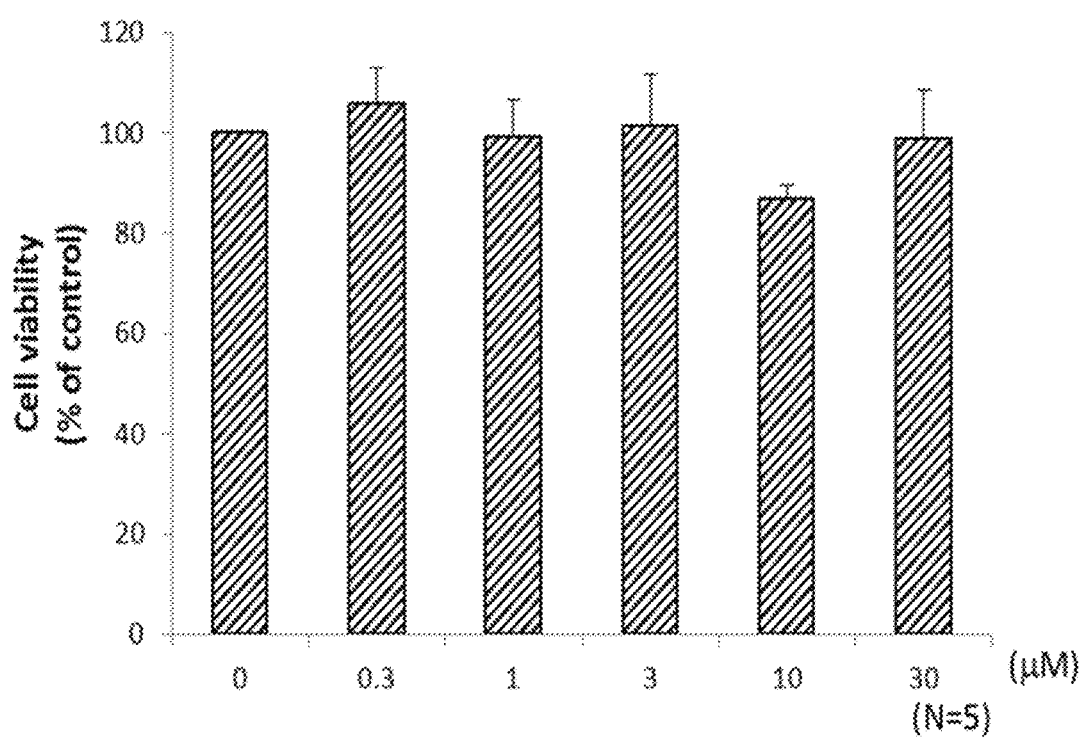
FIG. 7 shows the effect of L056 on cell viability in WI38 cells.

WI-38 lung fibroblasts were incubated with different concentrations of MPT0L056 (0.3, 1, 3 or 10 μM) for 2 hours before MTT-assay. FIG. 7 shows the effect of L056 on cell viability in WI38 cells. These data suggested that L056 did not affect cell viability.

Example 3 In Vive Efficacy: Bleomycin (BLM)-Induced Lung Fibrosis Mice Model Assay C57BL/6JNarl mice (8 weeks) were treated with bleomycin (BLM, 0.05 U/50 μl) or PBS (50 μl) by endotracheal administration. L056 (25, 50, 100 mg/kg/day, q.d.) and pirfenidone (200 mg/kg/day, q.d.) were administered orally to bleomycin-treated mice from 10 to 38 days after BLM treatment. On day 39, the mice were sacrificed, and the histologic analysis of lung tissue was performed by hematoxylin-eosin (H&E) staining (original magnification, ×100).

The results of MPT0L056 in reducing refibrosis score are shown in below table.

| Group | Mean ± SEM | Efficacy % |
|---|---|---|
| PBS | 1.42 ± 0.13 | |
| BLM | 5.19 ± 0.19 | |
| BLM + L056 25 mg | 3.27 ± 0.03 | 50.94% |
| BLM + L056 50 mg | 2.03 ± 0.21 | 83.90% |
| BLM + L056 100 mg | 2.65 ± 0.17 | 67.38% |
| BLM + Esbriet 200 mg | 3.91 ± 0.21 | 34.08% |
| BLM + OFEV 60 mg | 3.62 ± 0.30 | 41.66% |

Figure 8A:
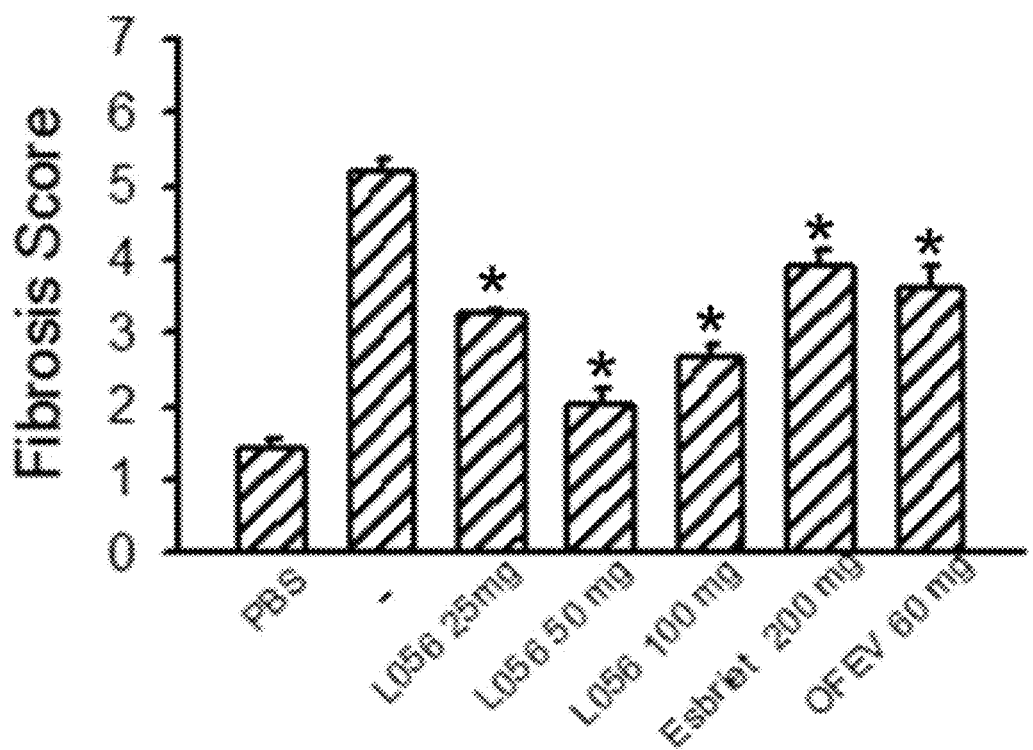
FIGS. 8(A) and 8(B) show the effects of L056 effect on fibrosis score of BLM-induced lung fibrosis in mice. C57BL/6 mice (8 weeks) were treated with bleomycin (BLM, 0.05 U/50 μl) or PBS (50 μl) by endotracheal administration. L056 (25, 50, 100 mg/kg/day, q.d.), nintedanib (OFEV) (200 mg/kg/day, q.d.) or esbriet (ie., pirfenidone) (200 mg/kg/day, q.d.) were administered orally to bleomycin-treated mice from 10 to 38 days after BLM treatment. On day 39, the mice were sacrificed and, the histologic analysis of lung tissue was performed by hematoxylin-eosin (H&E) staining (original magnification, ×100). Semiquantitative analysis of the histology showed that bleomycin administration led to elevated histology fibrosis score in the lungs.
Figure 8B:
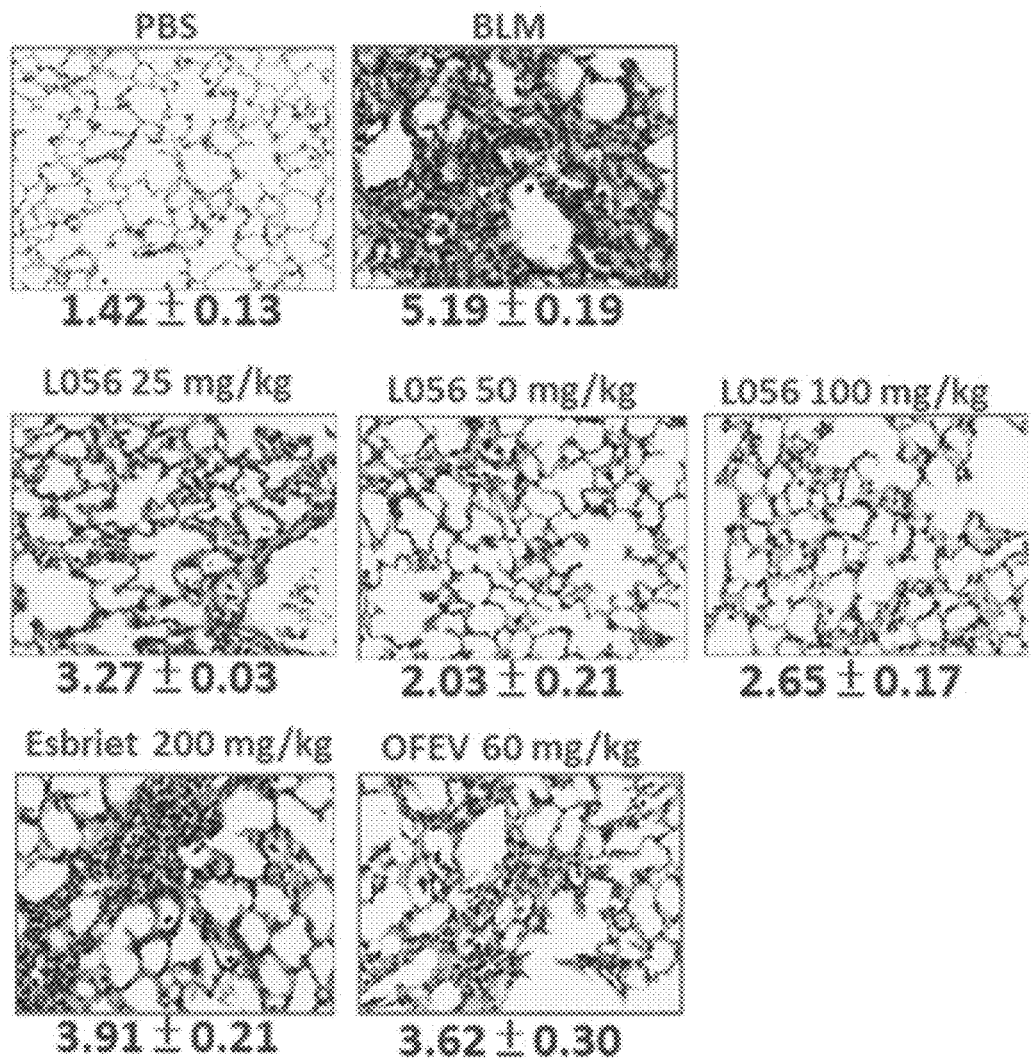
Figure 9A:
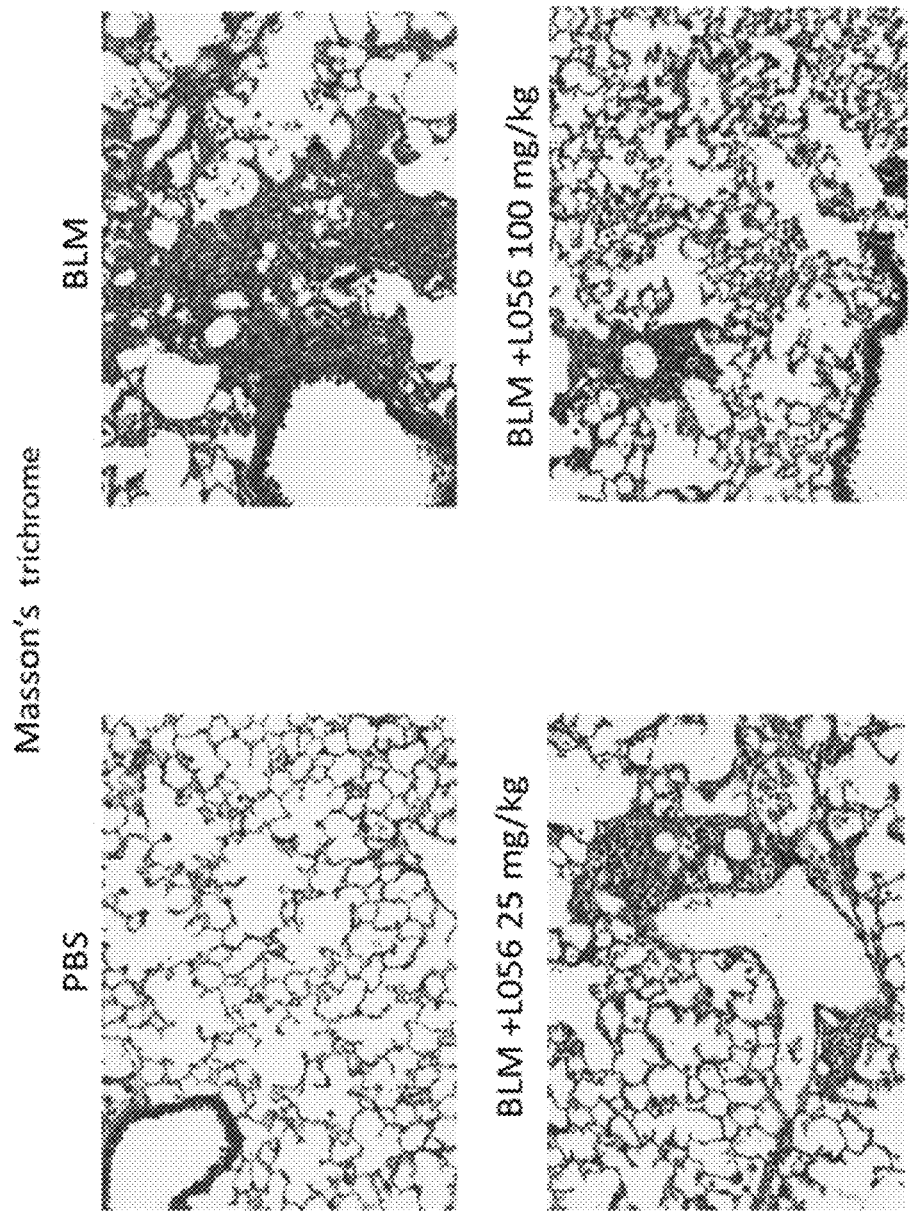
Figure 9B:
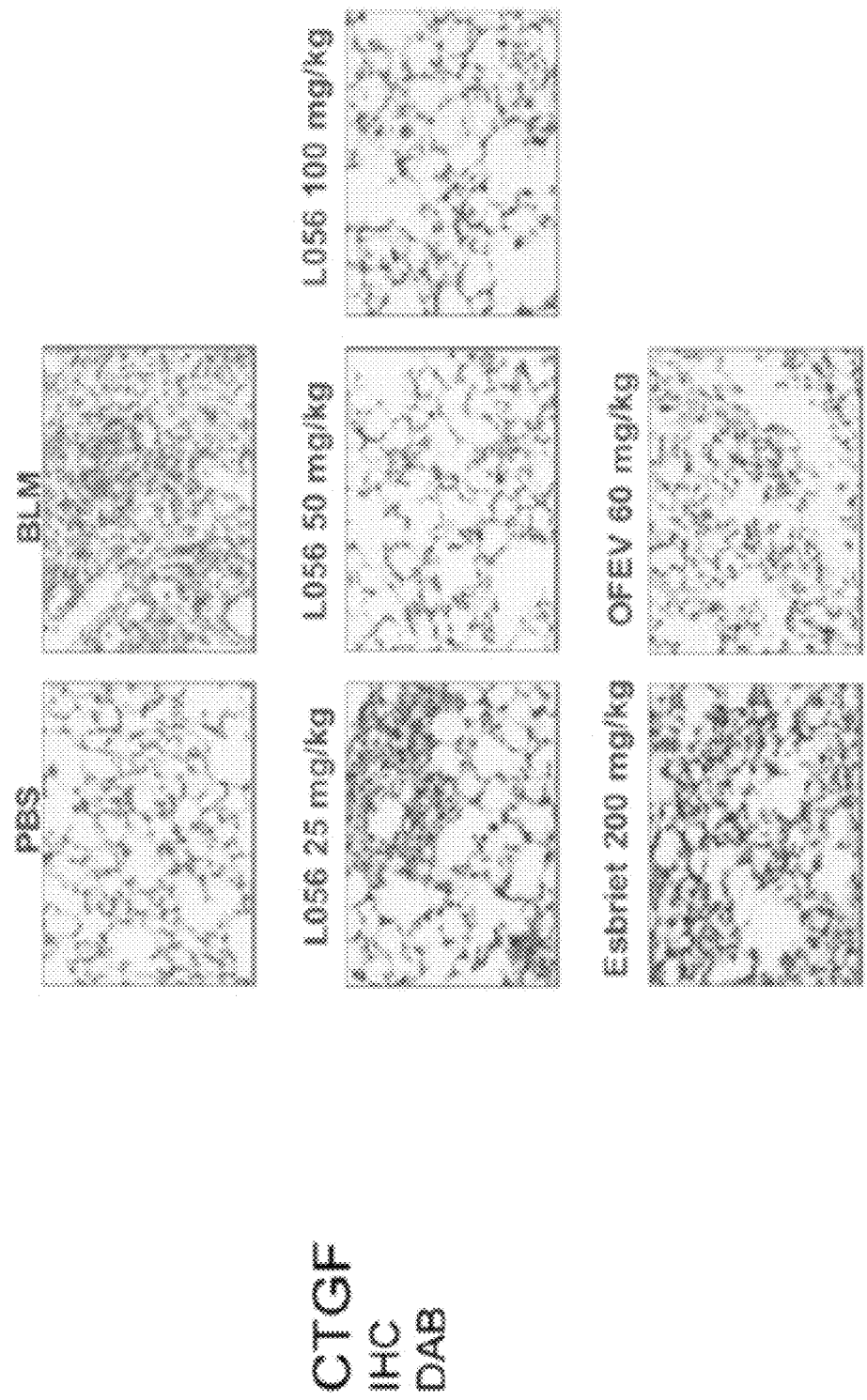
Figure 9C:
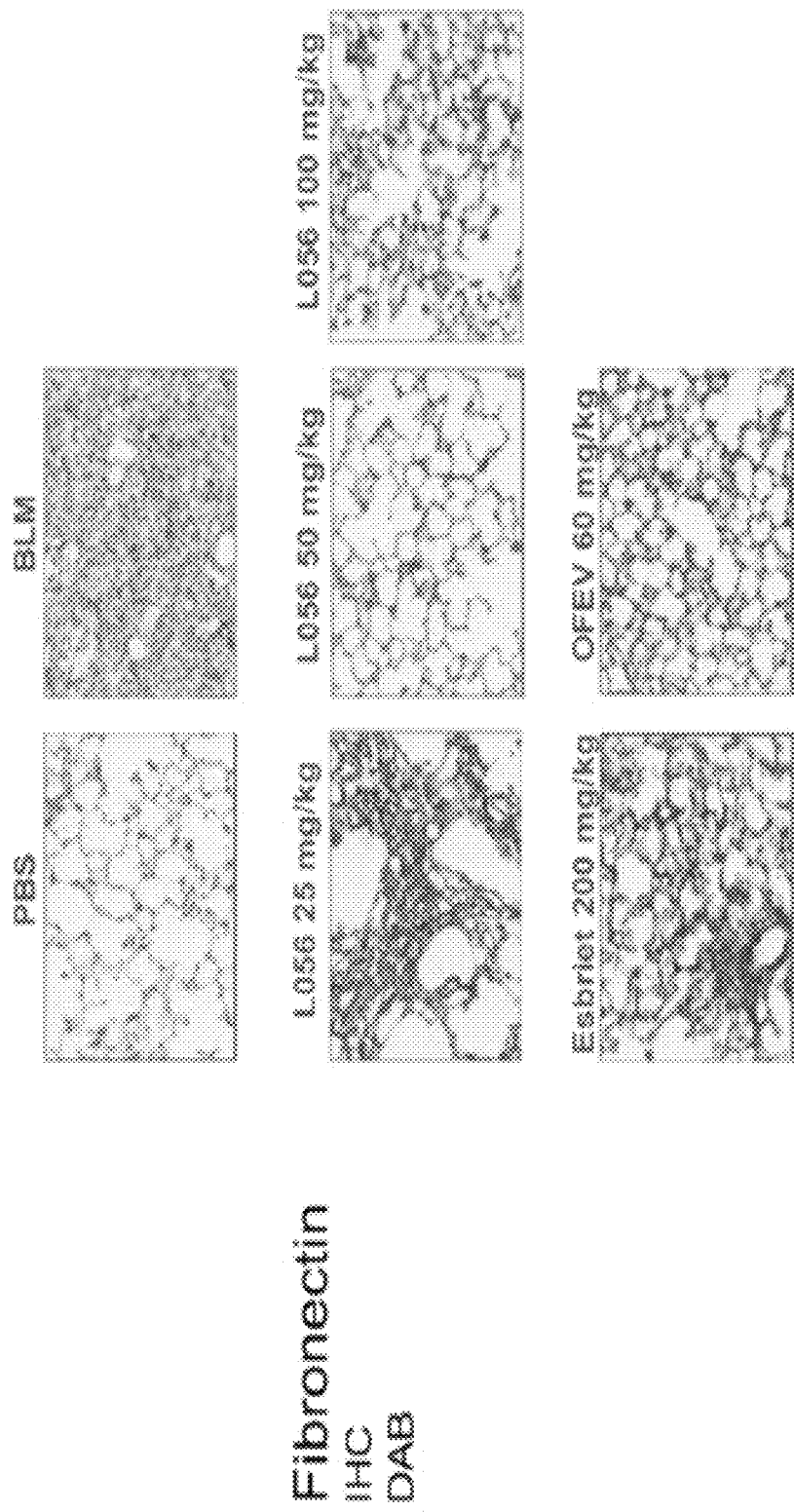

FIGS. 8A and 8B shows the antifibrotic effects of MPT0L056 on bleomydcin-induced pulmonary fibrosis in mice. The results show that MPT0L056 inhibits BLM-induced lung fibrosis in a dose-dependent manner (see FIG. 8(A)), and the efficacy of L056 in the inhibition is significantly higher than the PBS control (see FIG. 8(B)).

The pro-fibrogenic mediators, pro-fibrogenic mediators, collagen, CTGF, fibronectin and α-SMA were also examined and the results are shown in FIG. 9(A) to (D), respectively. These data suggested that pro-fibrogenic mediators expression were inhibited by L056 treatment in bleomycin-induced mice lung fibrosis model.

Example 4 Effect of MPT0L056 on CCl4-Induced Liver Fibrosis in Mice

Figure 10A:
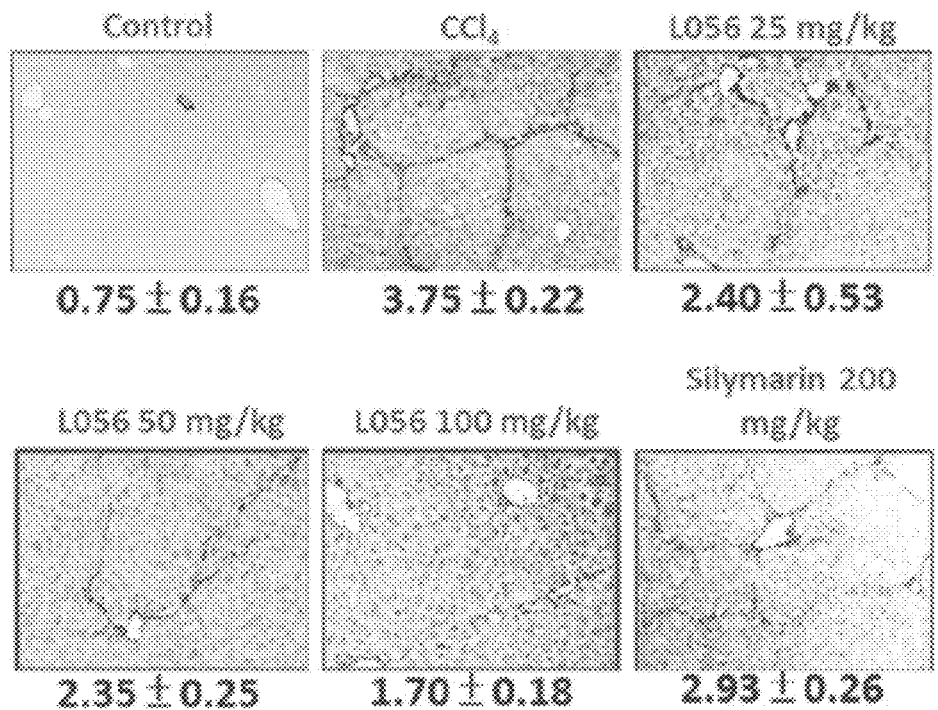
FIGS. 10(A) and 10(B) shows the effects of L056 on CC14-induced liver fibrosis in mice (therapeutic model).
Figure 10B:
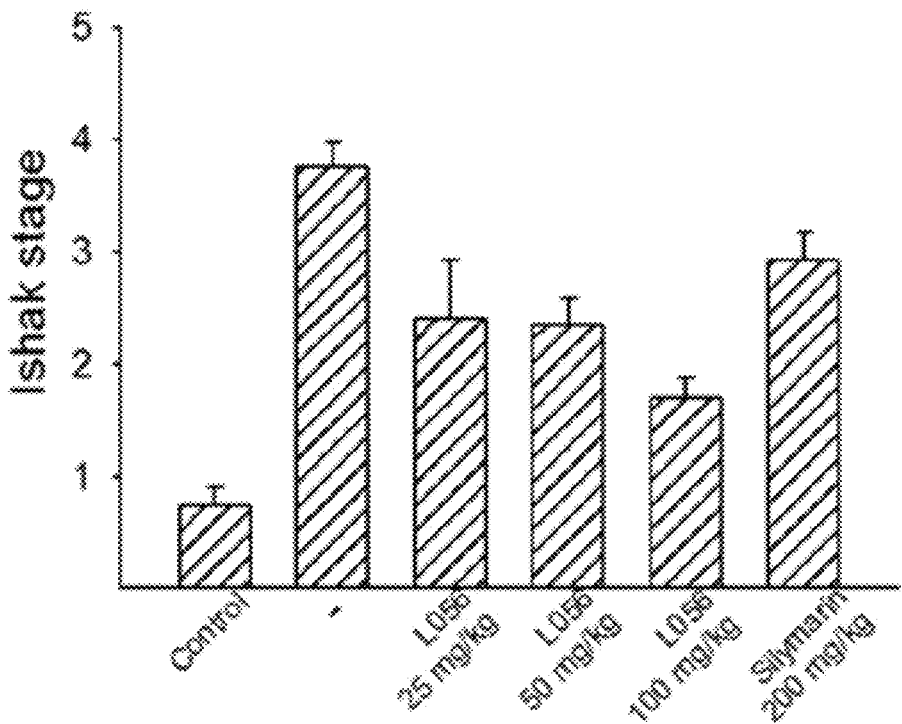
Figure 11:
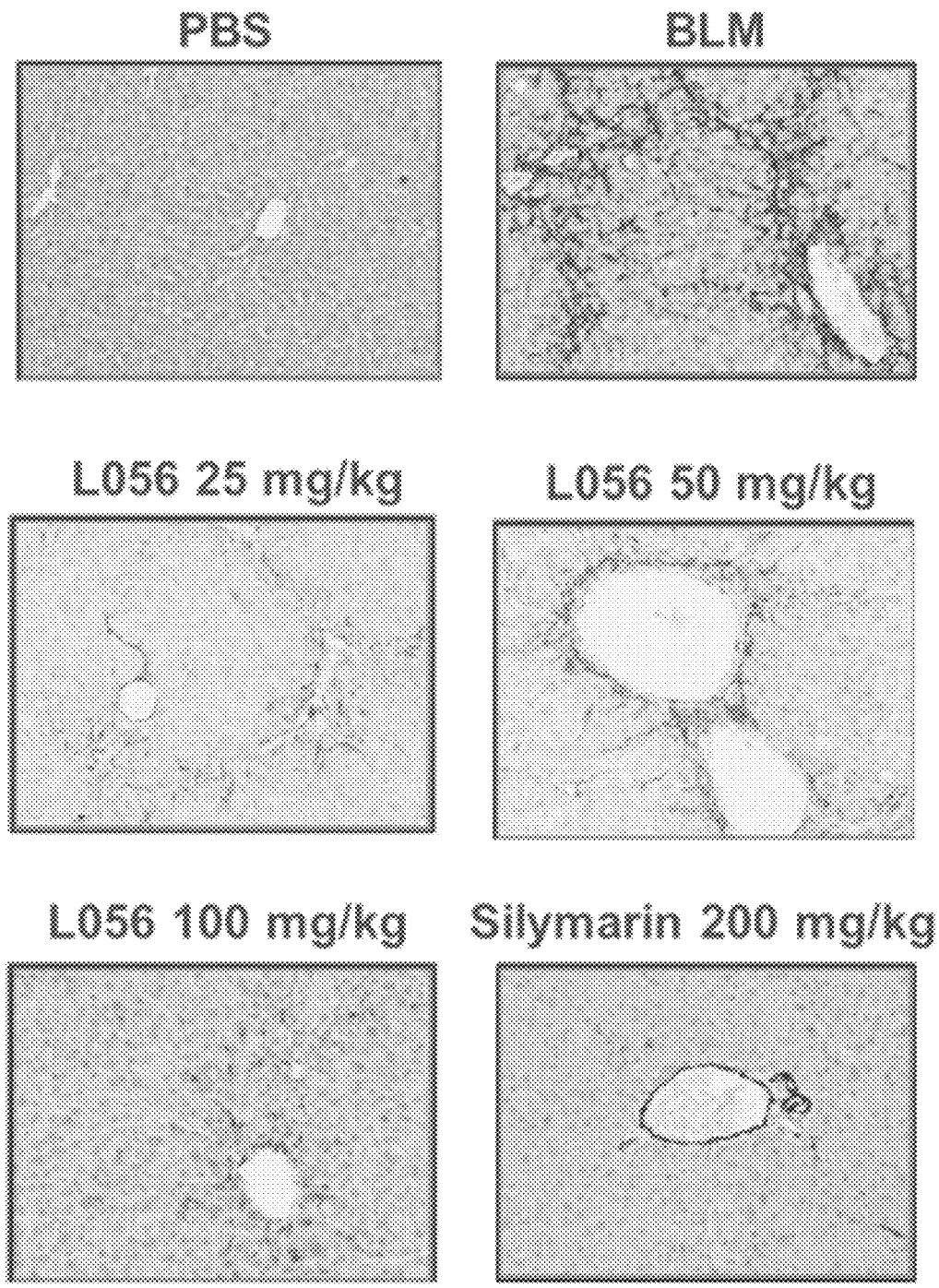

C57BL/6JNarl mice (8 weeks) were treated with CC14 (1 μl/μg/BW, q.w.) or PBS (1 μl/μg/BW, q.w.) by i.p. injection for 6 weeks. MPT0L056 (25, 50 and 100 mg/kg/day, q.d.) and silymarin (200 mg/kg/day, q.d.) were administered orally to CC14-injected mice from 2 weeks to 6 weeks. On day 43, the mice were sacrificed, and the α-SMA analysis of liver tissue was performed by IHC staining (original magnification, x100) (see FIG. 11). FIGS. 10A and 10B shows the antifibrotic effects of MPT0L056 and silymarin on CC14-induced liver fibrosis in mice. FIG. 10(A) shows the results of sirius red stain. As shown in FIG. 10(B), the inhibition of MPT0L056 on CC14-induced liver fibrosis is dose-dependent, and the efficacy of MPT0L056 in inhibition is higher than silymarin. The results of MPT0L056 in reducing refibrosis score are shown in below table.

| Group | Mean ± SEM | Efficacy % |
|---|---|---|
| Control | 0.75 ± 0.16 | |
| $CCl_4$ | 3.75 ± 0.22 | |
| $CCl_4$ + L056 25 mg | 2.40 ± 0.53 | 45.00% |
| $CCl_4$ + L056 50 mg | 2.35 ± 0.25 | 46.67% |
| $CCl_4$ + L056 100 mg | 1.70 ± 0.18 | 68.33% |
| $CCl_4$ + Silymarin 200 mg | 2.93 ± 0.26 | 27.50% |

What is claimed is:

1. A method for treatment of or liver fibrosis in a subject, comprising administering an effective amount of a compound of 4-(((3-chloro-1,4-dioxo-1,4-dihydronaphthalen-2-yl)amino)methyl)-N-(pyridin-4-yl)benzamide, having the following formula:

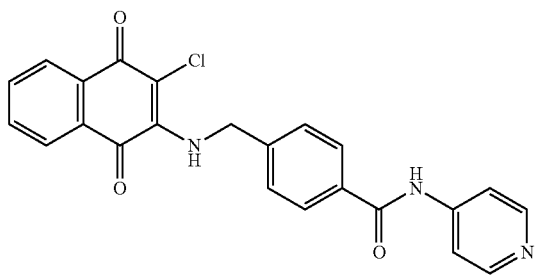

or a pharmaceutically acceptable salt, solvate or prodrug thereof as an active ingredient to the subject.

2. The method of claim 1, wherein the effective amount of the active ingredient used in the method of the invention ranges from about 1.5 mg/kg/day to about 20 mg/kg/day, about 5.0 mg/kg/day to about 15 mg/kg/day, or about 1.5 mg/kg/day to about 8 mg/kg/day.

3. The method of claim 1, wherein the active ingredient is further simultaneously, separately, or sequentially co-administered with a second anti-fibrosis agent.

4. The method of claim 3, wherein the second anti-fibrosis agent is pirfenidone, nintedanib, LOXL2 antibody, simtuzumab, IL-13 antibody, lebrikizumab, αVβ6 antibody, STX-100, CTGF antibody, FG-3019, tipelukast, MN-001, aerosol pirfenidone or GP-101.

* * * * *